(12) United States Patent
Gilbert et al.

(10) Patent No.: US 11,067,572 B2
(45) Date of Patent: *Jul. 20, 2021

(54) METHODS AND ASSAYS FOR FACTOR VIII ACTIVITY

(71) Applicants: PRESIDENT AND FELLOWS OF HARVARD COLLEGE, Cambridge, MA (US); THE U.S. GOVERNMENT AS REPRESENTED BY THE DEPARTMENT OF VETERANS AFFAIRS, Washington, DC (US)

(72) Inventors: Gary Eugene Gilbert, Cambridge, MA (US); Jialan Shi, Cambridge, MA (US); Valerie A. Novakovic, Cambridge, MA (US)

(73) Assignees: President and Fellows of Harvard College, Cambridge, MA (US); The U.S. Government as Represented by The Department of Veterans Affairs, Washington, DC (US)

( * ) Notice: Subject to any disclaimer, the term of this patent is extended or adjusted under 35 U.S.C. 154(b) by 136 days.

This patent is subject to a terminal disclaimer.

(21) Appl. No.: 16/173,693

(22) Filed: Oct. 29, 2018

(65) Prior Publication Data

US 2019/0064159 A1    Feb. 28, 2019

Related U.S. Application Data

(63) Continuation of application No. 15/036,199, filed as application No. PCT/US2014/064979 on Nov. 11, 2014, now Pat. No. 10,114,017.

(60) Provisional application No. 61/904,948, filed on Nov. 15, 2013.

(51) Int. Cl.
*G01N 33/554* (2006.01)
*G01N 33/86* (2006.01)
*G01N 30/60* (2006.01)
*G01N 33/543* (2006.01)

(52) U.S. Cl.
CPC ....... *G01N 33/554* (2013.01); *G01N 30/6047* (2013.01); *G01N 33/54326* (2013.01); *G01N 33/86* (2013.01); *G01N 2333/75* (2013.01); *G01N 2333/755* (2013.01); *Y10S 435/975* (2013.01)

(58) Field of Classification Search
CPC .. G01N 33/554; G01N 33/86; G01N 2333/75; G01N 2333/755; Y10S 435/975
See application file for complete search history.

(56) References Cited

U.S. PATENT DOCUMENTS

| | | |
|---|---|---|
| 5,506,112 A | 4/1996 | Lang |
| 5,773,228 A | 6/1998 | Reed |
| 5,807,686 A | 6/1998 | Wanger |
| 7,544,660 B2 * | 6/2009 | Lenting ............... C07K 14/755 514/1.1 |
| 2006/0024229 A1 | 2/2006 | Karp |
| 2007/0037235 A1 | 2/2007 | Lentz |
| 2009/0258834 A1 | 10/2009 | Hammond |
| 2010/0291603 A1 | 11/2010 | Owen |
| 2011/0177592 A1 | 7/2011 | Faustman |
| 2013/0029913 A1 | 1/2013 | Goodall |
| 2013/0116182 A1 | 5/2013 | Pratt |

FOREIGN PATENT DOCUMENTS

| | | |
|---|---|---|
| EP | 0457532 A1 | 11/1991 |
| WO | 2001/09188 A1 | 2/2001 |
| WO | 2013/120939 A1 | 5/2013 |

OTHER PUBLICATIONS

Philip et al. (Hepatology 2004 vol. 2, p. 1806-1815) (Year: 2004).*
Egler et al., "Kinetic parameters of monclonal antibodies ESH2, ESH4, ESH5, and ESH8 on coagulation factor VIII and their influence on factor VIII activity", J Mol Recognit 22: 301-306 (2009).
Gilbert et al., "Four Hydrophobic Amino Acids of the Factor VIII C2 Domain Are Constituents of Both the Membrane binding and von Willebrand Factor-binding Motifs", The Journal of Biological Chemistry 277(8) 6374-6381 (2002).
Gilbert et al., "Platlet binding sites for factor VIII in relation to fibrin and phosphatidylserine", Blood 126(10) 1237-1244 (2015).
Gilbert et al., "Platlet-derived Microparticles Express High Affinity Receptors for Factor VIII", The Journal of Biological Chemistry 266(26) 17261-17268 (1991).
Heijnen et al., "Activated Platelets Release Two Types of Membrane Vesicles by Surface Shedding and Exosomes Derived From Exocytosis of Multivesiculat Bodies and Alpha-Granules", Blood 94(11) 3791-3799 (1999).
Lu et al., "A membrane-interactive surface on the factor VIII C1 domain cooperates with the C2 domain for cofactos function", Blood 117(11) 3181-3189 (2011).
Phillips et al., "Fibrin stimulates platelets to increase factor VIIIa binding site expression", Journal of Thrombosis Haemostasis 2: 1806-1815 (2004).
Pipe et al., "Characterization of a genetically engineered inactivation-resistant coagulation factor VIII1", Proc Natl Acad Sci USA 94: 11851-11856 (1997).
Saenko et al., "Slow Release of Thrombin-cleaved Factor VIII from von Willebrand Factor by a Monoclonal and a Human Antibody is a Novel Mechanisms for Factor VIII Inhibition", The Journal of Biological Chemistry 271(44) 27424-27431 (1996).
Shi et al., "Thrombin-Stimulated Platelets Have Functional Binding Sites for Factor VIIIa That Are Distinct From Phosphatidylserine", Blood 122: 3582 (2013). (Retrieved from http://www.bloodjournal.org/content/122/21/3582).
Ye et al., "Recreation of the terminal events in physiologicl integrin activation". J Cell Biol 188(1) 157-173 (2010).

* cited by examiner

*Primary Examiner* — Changhwa J Cheu
(74) *Attorney, Agent, or Firm* — Nixon Peabody LLP; David S. Resnick; Mark J. FitzGerald

(57) ABSTRACT

The methods and compositions described herein relate to the measurement of factor VIII (fVIII) levels and/or activity.

7 Claims, 10 Drawing Sheets

METHODS AND ASSAYS FOR FACTOR VIII ACTIVITY

CROSS-REFERENCE TO RELATED APPLICATIONS

This application is a Continuation Application of U.S. application Ser. No. 15/036,199 filed May 12, 2016, which is a 35 U.S.C § 371 National Phase Entry Application of International Application No. PCT/US2014/064979 filed on Nov. 11, 2014, which designates the U.S. and which claims benefit under 35 U.S.C. § 119(e) of U.S. Provisional Application No. 61/904,948 filed Nov. 15, 2013, the contents of which are incorporated herein by reference in their entirety.

TECHNICAL FIELD

The invention relates to methods and assays for measuring factor VIII activity in a sample.

BACKGROUND

Factor VIII is a plasma glycoprotein that is essential for normal hemostasis. Defective or absent factor VIII causes hemophilia A, a life-threatening bleeding disorder. Because the gene for factor VIII resides on the X chromosome, the disease occurs almost exclusively in males, the sons of mothers with one defective factor VIII gene.

In the absence of therapy, hemophilia A is usually fatal prior to the age of reproduction. However, intravenous infusion of factor VIII alleviates the bleeding risk. In developed countries patients are routinely treated with pharmaceutical factor VIII so that the life-span for hemophilia A patients now approaches the life span of unaffected patients.

SUMMARY

The methods and assays described herein are based, in part, on the discovery that platelets stimulated under physiological conditions comprise binding sites for factor VIII (fVIII) that are independent of phosphatidylserine. This differs from the stimulation of platelets by a non-physiological agonist, such as a calcium ionophore, which leads to exposure of many fVIII binding sites on the surface of platelets. Thus, provided herein are methods, assays, and kits for measuring fVIII activity under conditions that are more physiologically relevant. In particular, the replacement of phospholipid vesicles currently employed in the standard fVIII assays can provide more reliable measurement of fVIII activity for clinical diagnosis of fVIII deficiency and monitoring of therapy with fVIII product infusions, as well as providing for more accurate assays of the activity of pharmaceutical preparations of fVIII, including engineered fVIII preparations, for which current assays are known to have poor predictive value. The replacement of phospholipid vesicles having high phosphatidylserine concentration in the current fVIII assays with platelet membrane-comprising or mimetic compositions described herein is also expected to enhance the reliability of fVIII activity remaining in individuals who express anti-fVIII antibodies.

In one aspect, described herein is a method of measuring fVIII activity, the method comprising contacting a sample in which fVIII is to be measured with fibrin or fibrinogen (fibrin(ogen)) and a platelet membrane-comprising composition, under conditions that permit binding of fibrin(ogen) to the platelet membrane-comprising composition and permit binding of fVIII in the sample to the fibrin(ogen), and detecting activity of fVIII.

In one embodiment, the platelet membrane-comprising composition comprises isolated platelets.

In another embodiment, the platelets are thrombin-activated platelets.

In another embodiment, the platelet membrane-comprising composition comprises a platelet membrane fraction comprising gpIIbIIIa ($\alpha II_b \beta 3$ integrin).

In another embodiment, the platelet membrane-comprising composition comprises phospholipid vesicles.

In another embodiment, the contacting is performed in the presence of Factor IXa (fIXa) and Factor X (fX).

In another embodiment, detecting activity of fVIII comprises detecting cleavage of a chromogenic fXa substrate by fXa.

In another embodiment, detecting activity of fVIII comprises a plasma-based clotting assay and/or use of a fibrometer and/or use of a thromboelastometry device.

In another embodiment, detecting activity of fVIII bound to fibrin(ogen) is distinguished from fVIII that is not bound to fibrin(ogen) through the addition of a monoclonal antibody that selectively interferes with fVIII binding to fibrin (ogen).

In another aspect, described herein is a method of measuring partitioning of fVIII between fibrin(ogen) and von Willebrand factor (vWf), the method comprising: contacting blood or plasma in which partitioning is to be measured with a solid support having vWf binding matrix immobilized thereupon under conditions that permit binding of vWf to fVIII; separately measuring fVIII activity bound to the solid support via vWF and fVIII activity remaining in suspension after the blood or plasma is contacted with the support, thereby determining the proportion of fVIII bound to vWF; contacting blood or plasma from the same source with a solid support having fibrin(ogen) matrix immobilized thereupon under conditions that permit binding of fibrin(ogen) to fVIII; separately measuring fVIII activity bound to the solid support via fibrin(ogen) and fVIII activity remaining in suspension after the blood or plasma is contacted with the support, thereby determining the proportion of fVIII bound to fibrin(ogen); whereby the partitioning of fVIII between vWf and fibrin(ogen) is measured.

In one embodiment, either or both of vWf and fibrin (ogen) are immobilized to the solid support via an antibody that specifically binds vWf or fVIII, respectively.

In another embodiment, the solid support comprises a column matrix.

In another embodiment, contacting with a solid support comprises passing the sample over a column comprising the solid support.

In another embodiment, the solid support comprises agarose (e.g., SEPHAROSE, GE Healthcare, Inc.) or polystyrene beads.

In another embodiment, after the contacting, the solid support is washed with a buffer solution to remove unbound fVIII.

In another embodiment, washing of the solid support comprises a gradient sedimentation step.

In another aspect, described herein is a method of measuring the partitioning of fVIII between binding to von Willebrand factor and binding to fibrin(ogen) in a liquid sample, the method comprising contacting a solid support comprising fibrinogen or fibrin with the sample, removing the liquid sample from the solid support, and measuring fVIII activity bound to the support versus fVIII activity remaining in the liquid sample, wherein fVIII bound to the support partitions with fibrin(ogen) and fVIII remaining in solution is free or partitions with von Willebrand factor.

In one embodiment, either or both of vWf and fibrin(ogen) are immobilized to the solid support via an antibody that specifically binds vWf or fVIII, respectively.

In another embodiment, the solid support comprises a column matrix.

In another embodiment, contacting with the solid support comprises passing the sample over a column comprising the solid support.

In another embodiment, the solid support comprises magnetic beads, agarose beads or polystyrene beads.

In another embodiment, after the contacting, the solid support is washed with a buffer solution to remove unbound fVIII.

In another embodiment, washing of the solid support comprises a gradient sedimentation step.

In another aspect, described herein is a method of measuring the partitioning of fVIII between binding to von Willebrand factor and binding to fibrin(ogen) in a liquid sample, the method comprising contacting a solid support comprising an antibody that specifically binds fVIII with the sample, removing the solid support, and measuring the amount of von Willebrand factor and the amount of fibrin(ogen) bound to the support together with fVIII.

In one embodiment, the solid support comprises magnetic beads.

In another embodiment, the solid support comprises agarose beads.

In another embodiment, the solid support comprises polystyrene beads.

In another embodiment, the von Willebrand factor and fibrin(ogen) bound is measured by flow cytometry using fluorescently labeled antibodies that specifically bind von Willebrand factor and fibrin(ogen), respectively.

In another embodiment, the solid support is separated from the liquid sample by magnetic force.

In another embodiment, the solid support is separated from the liquid by sedimentation.

Also described herein are kits for measuring fVIII activity, the kit comprising: fibrin(ogen); a platelet membrane-comprising composition; Factor IXa; Factor X; and packaging materials therefor.

In one embodiment, the kit further comprises a chromogenic fXa substrate.

In another embodiment, the fibrin(ogen) is in association with the platelet membrane-comprising composition.

In another embodiment, the platelet membrane-comprising composition comprises activated platelets.

In another embodiment, the platelet membrane-comprising composition comprises activated gpIIbIIIa incorporated into a membrane composition.

Also described herein are kits for detecting the fraction of fVIII bound to von Willebrand factor vs. fibrin(ogen) wherein the kits comprise: a solid support having monoclonal antibodies that specifically bind fVIII immobilized thereupon; a device for separating the beads from blood or plasma, fluorescently labeled detection antibodies that specifically bind fibrin(ogen) and von Willebrand factor, respectively; calibrated control beads; and packaging materials therefor. The method of separating the beads from blood or plasma can comprise, e.g., a magnet or sedimentation.

BRIEF DESCRIPTION OF THE FIGURES

FIG. 4A depicts a graph of experiments in which various concentrations of factor VIII-fluor were incubated with soluble fibrin immobilized on anti-fibrinogen-Superose beads. After 10 min. bound factor VIII was evaluated by flow cytometry. Displayed results represent mean±range of duplicates for a single experiment representative of 5 experiments. Saturable binding of factor VIII-fluor was observed. FIG. 4B depicts a graph of an experiment in which various concentrations of VWF were incubated with 4 nM factor VIII-fluor for 15 min. prior to mixing with immobilized fibrin-anti-fibrinogen-Superose beads. Data are from a single experiment representative of 5 experiments. VWF inhibited factor VIII binding to fibrin. FIG. 4C depicts a graph of an experiment in which various concentrations of factor VIII-C2 were incubated with factor VIII-fluor prior to mixing with fibrin-anti-fibrinogen-Superose beads. Experiments were performed in tris-buffered saline containing 0.02 M NaCl. Factor VIII-C2 competed with factor VIII-fluor for binding to immobilized fibrin. Results are from a single experiment representative of three experiments. Displayed data are corrected for measured background fluorescence with control beads lacking fibrin (FIG. 5A) Various concentrations of fibrinogen were mixed with fVIII, factor IXa, factor X, and phospholipid vesicles prior to the simultaneous addition of thrombin (1 u/ml) and $Ca^{++}$ (1.5 mM). The reaction was stopped after the minutes by addition of EDTA and factor Xa measured with chromogenic substrate S-2765. Fibrin increased activity approx. 3.5-fold. The degree of enhancement of factor Xase activity by 20 μg/ml fibrin was evaluated with phospholipid vesicles of varying phosphatidylserine (PS) content (FIG. 5B). All vesicles had 10% PE with the balance as PC. Activity is displayed as the ratio of activity with fibrin/activity without fibrin Enhancement was greatest with 4% PS vesicles.

FIG. 6A depicts a graph of an experiment in which factor VIII-fluor, 4 nM, was incubated with 0.75 μg/ml ESH4 or 0.75 μg/ml ESH8 for 1 hr prior to mixing with fibrin-anti-fibrin-Superose or control beads lacking fibrin. Results are from a single experiment representative of 3 experiments. ESH4 and ESH8 decreased binding to below control levels (*) observed when factor VIII-fluor was incubated with control Superose beads. FIG. 6B depicts a graph of an experiment in which factor VIII was incubated with 10 μg/mL ESH4 or ESH8 for 1 hr at 23° C. prior to addition of factor IXa, factor X, thrombin, and Ca$^{++}$ as indicated in the legend to FIGS. 5A-5B. In the absence of antibodies, addition of 10 μg/ml fibrin increased Xase activity about 2-fold. Fibrin did not increase activity in the presence of ESH4 or ESH8 above the levels observed in the absence of fibrin. Results are from a single experiment representative of 4 experiments (FIG. 6A) and are mean±SD for 4 experiments. FIG. 6B is a bar graph showing the effect of anti-fVIII monoclonal antibodies on fVIII binding to fibrin and fibrin enhancement of factor Xase function.

FIG. 7A depicts a graph of an experiment in which factor VIII-fluor was incubated with 14 μg/ml ESH8 prior to mixing with platelets stimulated by thrombin. Bound factor VIII was measured by flow cytometry. ESH8 decreased bound factor VIII by approx. 70%. FIG. 7B depicts a graph of an experiment in which various concentrations of ESH4 were incubated with 2 nM factor VIII-fluor for 5 min prior to addition of thrombin-stimulated platelets. Bound factor VIII was evaluated by flow cytometry after 5 min. ESH4 inhibited approx. 80% of factor VIII binding with a half-maximal effect at <0.5 μg/ml. FIG. 7C depicts a graph of an experiment in which ESH8 or ESH4, 10 μg/ml was mixed with factor VIII for 60 min. prior to addition of factor IXa, factor X, platelets, Ca++, and thrombin at the concentrations indicated above. ESH8 inhibited 84% of activity and ESH4 inhibited 78% of activity. To obtain average aggregate values, factor Xase activity was normalized to the value in the absence of ESH4 or ESH8 for each experiment. Results are from a single experiment representative of two experiments (FIG. 7A) and 3 experiments (FIG. 7B). FIG. 7C is mean±SD from 4 experiments each performed in duplicate.

FIG. 10A depicts a graph of an experiment in which inhibition of 1 unit/ml factor VIII activity by ESH4 and ESH8 was evaluated against a factor VIII concentration curve in re-constituted platelet-rich-plasma. Fibrin formation was initiated by addition of 70 pM factor XIa, thrombin activation peptides, and Ca++. A log linear plot demonstrates sensitivity to factor VIII concentration over a 4-log range in factor VIII concentration. ESH4 inhibited somewhat more activity than ESH8. Results are representative of 3 experiments performed in full and 5 performed with fewer factor VIII concentrations. FIG. 10B depicts a graph comparing residual factor VIII activity in various plasma-based activities. aPTT and 2-stage results represents mean±SD for published results in reference (44) weighted equally with results obtained in this laboratory using commercial aPTT and 2-stage reagents. Inhibition was also evaluated in reconstituted platelet-rich-plasma lacking von Willebrand factor (act Platelet (−VWF)). Results from this lab are from 4 experiments (aPTT, 2-stage), activated platelets mean±SD for 3 experiments, activated platelets w/o von Willebrand factor −1 experiment. The inset, with log x-scale illustrates the error bars and allows comparison with and without von Willebrand factor. FIG. 10C depicts a bar graph comparing residual factor VIII activity in the presence of 10 μg/ml ESH8. aPTT without von Willebrand factor (aPTT (−VWF)) is from reference (32). Values on activated platelets are mean±SEM for 2 experiments and 1 experiment for plasma lacking von Willebrand factor.

DETAILED DESCRIPTION

Figure 1A:
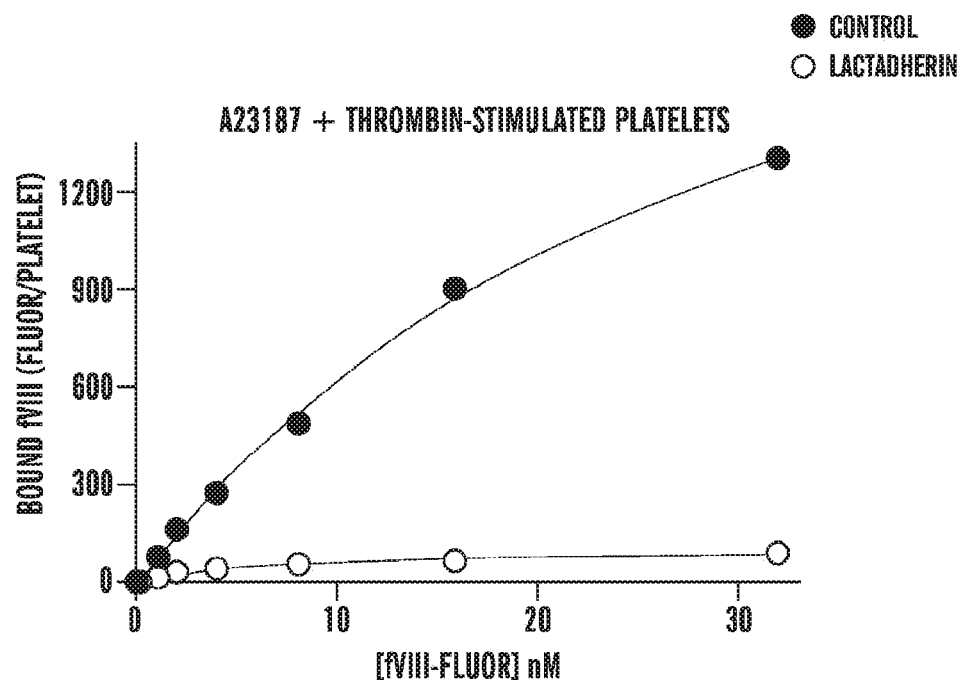
FIGS. 1A-1B are line graphs showing binding of fluorescein-fVIII to platelets in the presence of lactadherin. Platelets stimulated with 10 μM A23187+ thrombin have many fVIII binding sites and approximately 95% are blocked by 200 nM lactadherin. Platelets stimulated through the thrombin pathway express 3% of binding sites relative to sites activated by A23187. Lactadherin competes for approximately 25% of these sites while unlabeled fVIII competes for >70% of sites.

In one aspect, provided herein are methods, assays and kits for measuring fVIII activity in a sample. The methods and assays rely on the physiological activation of platelets by e.g., thrombin for exposing sites on the surface of platelets that bind fVIII independently of phosphatidylserine (e.g., platelet-bound fibrin or fibrinogen). The inventors have discovered, in part, that platelet stimulation by a calcium ionophore (a non-physiological agonist) leads to exposure of many binding sites comprised primarily of exposed phosphatidylserine, whereas platelets stimulated by thrombin (a physiological agonist) have binding sites that are comprised of platelet-bound fibrin or fibrinogen.

Definitions

All scientific and technical terms used in this application have meanings commonly used in the art unless otherwise specified. As used in this application, the following words or phrases have the meanings specified.

"Factor VIII activity" or "fVIII activity" is defined as the ability to function in the coagulation cascade, induce the formation of Factor Xa via interaction with Factor IXa on an activated platelet, and support the formation of a blood clot.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean ±1%.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Hemophilia A

Hemophilia A is an X-linked hemorrhagic disorder resulting from mutations in the gene encoding fVIII. Affected individuals commonly present spontaneous hemorrhages and prolonged bleeding after trauma or surgery. Severely affected subjects present with levels of fVIII that are lower than 1% of normal and comprise the majority of clinically symptomatic cases. The remaining patients have mild to moderate disease with factor levels of 1-30%. In this application, "Hemophilia A" refers to patients with less than 1% fVIII unless otherwise specified.

People with deficiencies in fVIII who are not treated with fVIII can suffer uncontrolled internal bleeding that may cause a range of serious symptoms, from inflammatory reactions in joints to early death. Severe hemophiliacs can be treated with infusion of human fVIII, which will restore the blood's normal clotting ability if administered with sufficient frequency and concentration. The classic definition of fVIII, in fact, is that substance present in normal blood plasma that corrects the clotting defect in plasma derived from individuals with hemophilia A.

Factor VIII (fVIII)

FVIII functions in an enzyme complex that converts the pro-enzyme, factor X, to the enzyme, factor Xa. FVIII, a pro-cofactor, is cleaved at at least two peptide bonds, to become an active cofactor (fVIIIa). FVIIIa binds to sites on a cell membrane and forms a complex with factor IXa, a serine proteinase. The membrane-bound complex of fVIIIa with factor IXa cleaves factor X with an efficiency that is at least 10,000-fold greater than factor IXa alone. The current literature indicates that phosphatidylserine is a critical constituent of fVIIIa binding sites.

FVIII circulates in plasma in complex with von Willebrand factor (vWf). Binding to von Willebrand factor decreases the rate at which fVIII is cleared from plasma and decreases the susceptibility of fVIII to degradation by enzymes within plasma. FVIII can dissociate from von Willebrand factor in three ways, prior to gaining activity. First, fVIII dissociates from von Willebrand factor in a slow dissociation process to maintain an equilibrium dissociation constant of 0.1-0.2 nM. Second, fVIII dissociates more rapidly from von Willebrand factor that has bound to collagen or other molecules. Third, fVIII is cleaved by thrombin at a scissile bond at amino acid 1689 of fVIII. Upon cleavage oat this site, an acidic peptide is released and fVIII dissociates rapidly from von Willebrand factor. Provided herein are methods and assays based on the discovery that a second plasma protein, fibrinogen, binds fVIII and that fVIII in complex with fibrinogen cannot bind von Willebrand factor.

Factor VIII Assays

Current standard practice for measuring fVIII activity typically uses a "one-stage" or a "two-stage" assay.

One stage assays rely on mixture of subject plasma with plasma that is deficient in fVIII. The plasma is incubated with an activator and then calcium is added to initiate coagulation. The length of time until clot formation is inversely related to the quantity of fVIII. The assay can be used to evaluate the factor activity of pharmaceutical fVIII concentrations. The fVIII product is diluted to various degrees and mixed with fVIII deficient plasma. In either case, the quantity of fVIII is evaluated by comparison to dilutions of normal plasma (with fVIII).

Two stage assays rely on mixture of subject plasma with a mixture containing factor IXa (fIXa), factor X (fX) and phospholipid vesicles. Calcium is added to permit the fVIIIa-fIXa complex to form and activate fX to fXa. After an interval, the reaction is quenched. The quantity of fX formed, proportional to fVIII activity, is measured by the rate at which a chromogenic substrate is cleaved by fXa.

Both assay types rely on phospholipid vesicles to provide a membrane surface on which the fVIIIa-fIXa complex assembles. The composition of the phospholipid mixture is proprietary for some preparations, but is generally know to be comprised of a mixture of phosphatidylserine, phosphatidylcholine, and phosphatidylethanolamine. The one and two-stage assays described above provide different values for activity of engineered products. This has led to uncertainty in the biologic activity and the appropriate doses for patients. This problem has been recognized by the FDA, the NIH, and pharmaceutical companies.

Such assays are described in e.g., Manucci and Tripodi, "Factor VIII clotting activity". E.C.A.T. assay procedures, London: Kluwer Academic Publishers, 1999; endogenous thrombin potential analysis, as described in Hemker et al., "The thrombogram: monitoring thrombin generation in platelet-rich plasma," Thrombosis and haemostasis, vol. 83:589-591, among others.

Fibrinogen

Fibrinogen is a major plasma protein, present at approximately 200-fold higher concentration than von Willebrand factor. Fibrinogen has several proven physiologic roles. Thrombin cleaves fibrinogen to form fibrin and the fibrin molecules self assemble to form a gel, the material responsible for physical properties of a blood clot. Fibrinogen is a critical ligand for the $\alpha_{IIb}\beta_3$ integrin of platelets, functioning as a bridge between platelets as they aggregate. Fibrin has known binding affinity for thrombin, vitronectin, and plasmin and these proteins influence the durability of blood clots. Fibrinogen is commercially available, e.g., from Sigma-Aldrich (see, e.g., Catalog Nos. F38799 and F4883, both human fibrinogen products).

Other Clotting Factors, Substrates and Equipment

Other factors of use in the methods, compositions and kits described herein include, for example, human fIX and fIXa. Human fIX is commercially available, e.g., from Alpha Therapeutic (ALPHANINE SD™), Pfizer (BENEFIX™), CSL Behring (MONONINE™). fIX is converted to fIXa in plasma.

Human fX is commercially available, e.g., from Sino Biologicals, Inc., Daxing, China (see, e.g., catalog No. 11076-H08B and No. HG-11076-M) and from Enzyme Research Laboratories, Inc. (see, e.g., catalog No. HFX 1010).

Chromogenic fXa substrates useful in assays as described herein are commercially available. For example, Sigma-Aldrich sells chromogenic fXa substrate $CH_3OCO$-D-CHA-Gly-Arg-pNA-AcOH under Catalog No. F-3301, and a thrombin generation chromogenic substrate, $\beta$-Ala-Gly-Arg-p-nitroanilide diacetate under Catalog No. T3068. Chromogenix (Milan, IT) sells a chromogenic fXa substrate as Catalog No. S-2765. Abcam (Cambridge, Mass.) also sells a Factor X Human Chromogenic Activity Assay kit under Catalog No. ab108833, which measures activated fX in plasma and culture medium, among other sample types.

Monoclonal antibodies specific for fibrin(ogen) and for vWf are commercially available, e.g., from Santa Cruz Biotech. Kits for coupling antibodies and other peptide or polypeptide agents to solid supports, e.g., beads, are also commercially available, e.g., from Life Technologies, Inc. and from Abcam, Inc.

Block Scientific sells the BBL Fibrometer coagulation analyzer made by BD Diagnostic Systems.

Thromboelastometry provides another method of measuring clotting and the effects of clotting factors. Thromboelastometry, also referred to as rotational thromboelastometry or rotational thromboelastography, is a viscoelastic method for haemostasis testing in whole blood, and permits investigation of the interaction of coagulation factors, their inhibitors, anticoagulant drugs, blood cells, specifically platelets, during clotting and subsequent fibrinolysis. The rheological conditions mimic the sluggish flow of blood in veins. Thromboelastometry is performed, for example, with the ROTEM whole blood analyzer (Tem Innovations GmbH, Munich). For such assays, blood (300 µl, anticoagulated with citrate) is placed into a cuvette. A disposable pin is attached to a shaft which is connected with a thin spring and slowly oscillates back and forth. The signal of the pin suspended in the blood sample is transmitted via an optical detector system. The test is started by adding appropriate reagents. The instrument measures and graphically displays the changes in elasticity at all stages of the developing and resolving clot.

Platelet Membrane-Comprising Compositions:

Various methods and compositions described herein use platelet membrane-comprising compositions that permit the assembly of an active enzyme complex that activates fX to fXa. The membrane-comprising compositions applicable to the methods and compositions described herein have the ability to bind fibrin or fibrinogen, e.g., via the gpIIbIIIa glycoprotein complex associated with the membrane composition, which is a platelet receptor for fibrinogen. The activated complex is formed by the association of glycoprotein IIb with glycoprotein IIIa in the context of a phospholipid membrane. As such, platelet membrane-comprising compositions as described herein can include whole platelets, e.g., human donor platelets, including thrombin-activated platelets, as well as membrane fractions made from them that include the gpIIbIIIa complex and retain the ability to bind fibrinogen. Methods for the isolation of platelets and platelet membrane fractions are well known. As one example, Heijnen et al., Blood 94: 3791-3799 (1999), which is incorporated herein by reference in its entirety, describes methods of platelet isolation. This reference also describes membrane microvesicles released from activated platelets that are enriched for glycoproteins and support the formation of the fX/prothrombin complex. The reference describes how to isolate the membrane microvesicles, as well as analysis of them using flow cytometry. Microvesicles of the kind described by Heijnen et al. are specifically contemplated for use as platelet membrane-comprising compositions as needed in methods and compositions as described herein. Other platelet membrane-containing fractions that support the methods and compositions described herein include, for example, the platelet-derived microparticles described by Gilbert et al., J. Biol. Chem., 266: 17261-17268 (1991), also incorporated herein by reference in its entirety.

It is contemplated that rather than requiring the phospholipids be isolated from platelets, synthetic or purified phospholipids can be formulated in association with gpIIbIIIa and also be used in methods and compositions as described herein in place of membrane compositions isolated from platelets. The critical factor for such compositions, which mimic platelet membranes ("platelet membrane mimetics") is that they permit binding of fibrin to gpIIbIIIa, and that the phospholipid used contains at least 2% phosphatidylserine. Among other possibilities, the gpIIbIIIa/phospholipid compositions can be formulated, e.g., as liposomes of nanodiscs. The preparation of liposomes and nanodiscs comprising active gpIIbIIIa is described, for example, by Ye et al. J. Cell Biol. 188: 157-173 (2010), which is incorporated herein by reference in its entirety. It is also contemplated, for example, that other membrane-associated proteins, engineered to specifically bind fibrinogen, e.g., by inclusion of an antibody domain that binds fibrinogen, could also support the assembly of the fVIII-fibrinogen complex involved in the fVIII assay methods described herein.

Blood Coagulation Assays

Blood coagulation (clotting) assists homeostasis by minimizing blood loss. In vivo, clotting usually requires vessel damage, platelet aggregation, coagulation factors and inhibition of fibrinolysis. The coagulation factors have been reported to act through a cascade that relates vessel damage to formation of a blood clot. See generally L. Stryer, Biochemistry, 3rd Ed, W. H. Freeman Co., New York; A. G. Gilman et al., The Pharmacological Basis of Therapeutics, 9th Edition, McGraw Hill Inc., New York, pp. 1341-1359; and Mann, K. G. et al. (1992) Semin. Hematol. 29:213.

Initiation of blood coagulation arises from two distinct pathways: the intrinsic (contact) and extrinsic pathways. The intrinsic pathway can be triggered in vitro by contact of blood borne factor with artificial negatively charged surfaces such as glass. In contrast, the extrinsic pathway can be initiated in vivo or in vitro when tissue factor (TF) on a phospholipid surface, normally sequestered from the circulatory system, comes into contact with blood following injury. Both pathways are characterized by the assembly of multiple protein complexes on procoagulant surfaces, which serves to localize the response to the site of injury. See e.g, Mann, K. G. et al. (1990) Blood 76: 1; Mann, K. G. et al. (1992), supra.

Current theories of coagulation maintain that an interplay between the two pathways is required for efficient blood clotting. See e.g., S. I., Rapaport and L. V. M. Rao (1995) Throm. Haemost. 74: 7. The contact pathway has been further divided into early and late steps. These steps are typically associated with specific coagulation factors. It has been reported that hemophilia A, B and C are each correlated with deficiencies in the late contact pathway (fVIII, fIX, and fXI, respectively).

Many activities of the extrinsic and intrinsic tenases (fVIIIa-fIXa) and the prothrombinase complex are facilitated by activated platelets and other phospholipid membranes.

In clinical settings, citrated plasma isolates are the most widely used blood product for coagulation testing, due to prominence of the prothrombin time (PT) and activated partial thromboplastin time (aPTT) tests. The PT is the more convenient assay, and is performed by addition of a large quantity of thromboplastin to the citrated plasma, with subsequent initiation of the reaction by calcium addition. The time to clot formation is noted, which for most normal donors is typically about 10 to about 14 seconds. The aPTT test involves about a 3 to about 5 minute preincubation of the citrated plasma with a mixture of phospholipids and solids possessing negatively charged surfaces. The reaction is initiated by calcium addition, and the clot time for normal donors typically falls between 25 and 43 seconds. While well established in the clinical venue, neither assay is entirely suitable to mimic the physiological coagulation reaction in its entirety.

For example, while the PT measurement employs the physiologically relevant initiator TF and the assay is sensitive to Factors V, VII, X, and prothrombin (II), the concentration used is sufficiently high that the reaction is usually insensitive to deficiencies or abnormalities in coagulation Factors VIII or IX. Clotting occurs rapidly in normal individuals (about 10 to about 14 seconds), and errors in measurement on the order of seconds are a significant fraction of the total clot time. The PT is an effective assay for measuring clotting time of a blood sample.

The aPTT assay is also associated with problems. For example, since initiation proceeds through the early contact pathway members, Factor VII is bypassed in this reaction. As a result, this assay in insensitive to deficiencies or abnormalities in this biologically important coagulation factor. Additionally, most aPTT assays use plasma and are not compatible with whole blood. When the assay is used to monitor administration of anti-coagulants, the target range for prolongation of the clot time is between about 2.5 to about 3.5 times normal, or between about 25 and 49 seconds. There has been recognition that this time range is often too small to permit accurate analysis.

Solid Supports

In certain embodiments, it is desirable to measure the partitioning of fVIII between fibrinogen and von Willebrand factor. In one embodiment, von Willebrand factor is immobilized to a solid support. In another embodiment, fibrin or fibrinogen is immobilized to a solid support. In other embodiments, antibodies that specifically bind one factor/protein or another are immobilized on a solid support. Protein or peptide immobilization can be achieved using methods routine to those of ordinary skill in the art, and can be direct, e.g., by binding of the protein or peptide directly to the surface of the support, or, indirect, e.g., by binding through a linker (peptide or other chemical-based linkers) or by binding to an antibody immobilized on the support surface that recognizes and binds the desired factor or protein. In some embodiments, indirect binding provides advantages in activity of the bound protein/factor—while not wishing to be bound by theory, such effects are likely due to improved access of the linked factor or protein to its environment and accompanying lack of steric hindrances.

In some embodiments, the solid support comprises, for example, magnetic beads, SEPHAROSE or other agarose beads, a nitrocellulose membrane, a nylon membrane, a column chromatography matrix, a high performance liquid chromatography (HPLC) matrix or a fast performance liquid chromatography (FPLC) matrix for purification. As used herein, the term "magnetic bead" means any solid support that is attracted by a magnetic field; such solid supports include, without limitation, DYNABEADS™ (Life Technologies, Inc.), BIOMAG™ (Qiagen, Inc.), MPG7 (PureBiotech LLC), MAGNESPHERE™ (Promega, Inc.) Magnetic Particles, any of the MAGNA™ line of magnetizable particles (Millipore, Inc.), BIOMAG™ Superparamagnetic Particles (Qiagen, Inc.), or any other magnetic bead to which a molecule (e.g., a protein factor, fibrin(ogen) or antibody) may be attached or immobilized. In one embodiment, a magnet or magnetic field can be used to separate the target protein or factor, and those other proteins or factors complexed with it, from bulk solution or suspension.

Screening Assays

Screening assays as contemplated herein can be used to identify modulators, i.e., candidate or test compounds or agents (e.g., peptides, antibodies, peptidomimetics, small molecules (organic or inorganic) or other drugs) which modulate fVIII activity. In certain aspects a screen for agents that modulate the interaction between fVIII and fibrin(ogen) are of interest.

The term "candidate agent" is used herein to mean any agent that is being examined for ability to modulate the activity of fVIII. Although the method generally is used as a screening assay to identify previously unknown molecules that can act as a therapeutic agent, or an agent that modifies fVIII activity or fVIII interactions with fibrin(ogen), the screening described herein can also be used to confirm that an agent known to have such activity, in fact has the activity, for example, in standardizing the activity of the therapeutic agent. A candidate agent can be any type of molecule, including, for example, a peptide, a peptidomimetic, a polynucleotide, or a small organic molecule, that one wishes to examine for the ability to modulate a desired activity, such as, for example, increasing or prolonging fVIII activity. It will be recognized that the screening methods described herein are readily adaptable to a high throughput format and, therefore, the methods are convenient for screening a plurality of test agents either serially or in parallel. The plurality of test agents can be, for example, a library of test agents produced by a combinatorial method library of test agents. Methods for preparing a combinatorial library of molecules that can be tested for fVIII-modulating activity are well known in the art and include, for example, methods of making a phage display library of peptides, which can be constrained peptides (see, for example, U.S. Pat. Nos. 5,622,699; 5,206,347; Scott and Smith, Science 249:386-390, 1992; Markland et al., Gene 109:1319, 1991; each of which is incorporated herein by reference in their entireties); a peptide library (U.S. Pat. No. 5,264,563, which is incorporated herein by reference); a peptidomimetic library (Blondelle et al., Trends Anal. Chem. 14:8392, 1995; a nucleic acid library (O'Connell et al., supra, 1996; Tuerk and Gold, supra, 1990; Gold et al., supra, 1995; each of which is incorporated herein by reference in their entireties); an oligosaccharide library (York et al., Carb. Res., 285:99128, 1996; Liang et al., Science, 274:1520-1522, 1996; Ding et al., Adv. Expt. Med. Biol., 376:261-269, 1995; each of which is incorporated herein by reference in their entireties); a lipoprotein library (de Kruif et al., FEBS Lett., 399:232-236, 1996, which is incorporated herein by reference in their entireties); a glycoprotein or glycolipid library (Karaoglu et al., J. Cell Biol., 130:567-577, 1995, which is incorporated herein by reference); or a chemical library containing, for example, drugs or other pharmaceutical agents (Gordon et al., J. Med. Chem., 37:1385-1401, 1994; Ecker and Crooke, Bio/Technology, 13:351-360, 1995; each of which is incorporated herein by reference in their entireties).

Accordingly, the term "agent" as used herein in the context of screening means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but are not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest that modulates fVIII activity or pharmacokinetics, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof.

In certain embodiments, the candidate agent is a small molecule having a chemical moiety. Such chemical moieties can include, for example, unsubstituted or substituted alkyl, aromatic, or heterocyclyl moieties and typically include at least an amine, carbonyl, hydroxyl or carboxyl group, frequently at least two of the functional chemical groups, including macrolides, leptomycins and related natural products or analogues thereof. Candidate agents can be known to have a desired activity and/or property, or can be selected from a library of diverse compounds. Also included as candidate agents are pharmacologically active drugs, genetically active molecules, etc. Such candidate agents of interest include, for example, chemotherapeutic agents, hormones or hormone antagonists, growth factors or recombinant growth factors and fragments and variants thereof. Exemplary of pharmaceutical agents suitable for use with the screening methods described herein are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all of which are incorporated herein by reference in their entireties. Also included are toxins, and biological and chemical warfare agents, for example see Somani, S. M. (Ed.), "Chemical Warfare Agents," Academic Press, New York, 1992), the contents of which is herein incorporated in its entirety by reference. Candidate agents, such as chemical compounds, can be obtained from a wide variety of sources including libraries of synthetic or natural compounds, such as small molecule compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and can be used to produce combinatorial libraries. Known pharmacological agents can be subjected to directed or random chemical modifications, such as acylation, alkylation, esterification, amidification, etc. to produce structural analogs. Synthetic chemistry transformations and protecting group methodologies (protection and deprotection) useful in synthesizing the candidate compounds for use in the screening methods described herein are known in the art and include, for example, those such as described in R. Larock (1989) Comprehensive Organic Transformations, VCH Publishers; T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof, the contents of each of which are herein incorporated in their entireties by reference. Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233, the contents of each of which are herein incorporated in their entireties by reference. Libraries of candidate agents can also, in some embodiments, be presented in solution (e.g., Houghten (1992), Biotechniques 13:412-421), or on beads (Lam (1991), Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222: 301-310; Ladner supra.), the contents of each of which are herein incorporated in their entireties by reference. The test compounds or candidate agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233. Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.). The methods described herein further pertain to novel agents identified by the above-described screening assays.

Screening assays can be performed, for example, by performing a fVIII activity assay as described herein with a known or constant amount of active fVIII in the presence and absence of a candidate agent. A difference in fVIII activity in such an assay is indicative that the candidate agent modifies the process assayed. Varying the amount or type (e.g., wild-type, mutated, engineered) of fVIII used can determine whether the effect is directly upon fVIII or indirect.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated in their entireties herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Some embodiments of the technology described herein can be defined according to any of the following numbered paragraphs:

1. A method of measuring Factor VIII (fVIII) activity, the method comprising contacting a sample in which fVIII is to be measured with fibrin or fibrinogen (fibrin(ogen)) and a platelet membrane-comprising composition, under conditions that permit binding of fibrin(ogen) to the platelet membrane-comprising composition and permit binding of fVIII in the sample to the fibrin(ogen), and detecting activity of the fVIII.
2. The method of paragraph 1 wherein the platelet membrane-comprising composition comprises isolated platelets.
3. The method of paragraph 2 wherein the platelets are thrombin-activated platelets.
4. The method of paragraph 1 wherein the platelet membrane-comprising composition comprises a platelet membrane fraction comprising gpIIbIIIa.
5. The method of paragraph 1 wherein the platelet membrane-comprising composition comprises phospholipid vesicles.
6. The method of paragraph 1 wherein the contacting is performed in the presence of Factor IXa (fIXa) and Factor X (fX).
7. The method of paragraph 1 wherein detecting activity of fVIII comprises detecting cleavage of a chromogenic fXa substrate by fXa.
8. The method of paragraph 1 wherein detecting activity of fVIII comprises a plasma-based clotting assay and/or use of a fibrometer and/or use of a thromboelastometry device.
9. The method of paragraph 1 wherein detecting activity of fVIII bound to fibrin(ogen) is distinguished from fVIII that is not bound to fibrin(ogen) through the addition of a monoclonal antibody that selectively interferes with fVIII binding to fibrin(ogen).
10. A method of measuring partitioning of fVIII between fibrinogen and von Willebrand factor (vWf), the method comprising:

contacting blood or plasma in which partitioning is to be measured with a solid support having vWf immobilized thereupon under conditions that permit binding of vWf to fVIII;
separately measuring fVIII activity bound to the solid support via vWF and fVIII activity remaining in suspension after the blood or plasma is contacted with the support, thereby determining the proportion of fVIII bound to vWF;
contacting blood or plasma from the same source with a solid support having fibrin(ogen) immobilized thereupon under conditions that permit binding of fibrin(ogen) to fVIII;
separately measuring fVIII activity bound to the solid support via fibrin(ogen) and fVIII activity remaining in suspension after the blood or plasma is contacted with the support, thereby determining the proportion of fVIII bound to fibrin(ogen);
whereby the partitioning of fVIII between vWf and fibrin(ogen) is measured.
11. The method of paragraph 10 wherein either or both of vWf and fibrin(ogen) are immobilized to the solid support via an antibody that specifically binds vWf or fVIII, respectively.
12. The method of paragraph 10 wherein the solid support comprises a column matrix.
13. The method of paragraph 10 wherein the contacting with the solid support comprises passing the sample over a column comprising the solid support.
14. The method of paragraph 10 wherein the solid support comprises Sepharose or polystyrene beads.
15. The method of paragraph 10 wherein after the contacting, the solid support is washed with a buffer solution to remove unbound fVIII.
16. The method of paragraph 15 wherein washing of the solid support comprises a gradient sedimentation step.
17. A method of measuring the partitioning of fVIII between binding to von Willebrand factor and binding to fibrin(ogen) in a liquid sample, the method comprising contacting a solid support comprising fibrinogen or fibrin with the sample, removing the liquid sample from the solid support, and measuring fVIII activity bound to the support versus fVIII activity remaining in the liquid sample, wherein fVIII bound to the support partitions with fibrin(ogen) and fVIII remaining in solution is free or partitions with von Willebrand factor.
18. The method of paragraph 17 wherein either or both of vWf and fibrin(ogen) are immobilized to the solid support via an antibody that specifically binds vWf or fVIII, respectively.
19. The method of paragraph 17 wherein the solid support comprises a column matrix.
20. The method of paragraph 17 wherein the contacting with the solid support comprises passing the sample over a column comprising the solid support.
21. The method of paragraph 17 wherein the solid support comprises magnetic beads, agarose beads or polystyrene beads.
22. The method of paragraph 17 wherein after the contacting, the solid support is washed with a buffer solution to remove unbound fVIII.
23. The method of paragraph 22 wherein washing of the solid support comprises a gradient sedimentation step.
24. A method of measuring the partitioning of fVIII between binding to von Willebrand factor and binding to fibrin(ogen) in a liquid sample, the method comprising contacting a solid support comprising an antibody that specifically binds factor VIII with the sample, removing the solid support, and measuring the amount of von Willebrand factor and the amount of fibrin(ogen) bound to the support together with factor VIII.
25. The method of paragraph 24 wherein the solid support comprises magnetic beads.
26. The method of paragraph 24 wherein the solid support comprises agarose beads.
27. The method of paragraph 24 wherein the solid support comprises polystyrene beads.
28. The method of paragraph 24 wherein the von Willebrand factor and fibrin(ogen) bound is measured by flow cytometry using fluorescently labeled antibodies that specifically bind von Willebrand factor and fibrin (ogen), respectively.
29. The method of paragraph 24 wherein the solid support is separated from the liquid sample by magnetic force.
30. The method of paragraph 24 wherein the solid support is separated from the liquid by sedimentation.
31. A kit for measuring fVIII activity, the kit comprising:
fibrin(ogen);
a platelet membrane-comprising composition;
Factor IXa;
Factor X; and
packaging materials therefor.
32. The kit of paragraph 31 further comprising a chromogenic fXa substrate.
33. The kit of paragraph 31 wherein the fibrin(ogen) is in association with the platelet membrane-comprising composition.
34. The kit of paragraph 31 wherein the platelet membrane-comprising composition comprises activated platelets.
35. The kit of paragraph 31 wherein the platelet membrane-comprising composition comprises activated gpIIbIIIa incorporated into a membrane composition.
36. A kit for detecting the fraction of factor VIII bound to von Willebrand factor vs. fibrin(ogen) wherein the kit comprises:
a solid support having monoclonal antibodies that specifically bind fVIII immobilized thereupon;
a device for separating the beads from blood or plasma,
fluorescently labeled detection antibodies that specifically bind fibrin(ogen) and von Willebrand factor, respectively;
calibrated control beads; and
packaging materials therefor.

EXAMPLES

Example 1

Thrombin-Stimulated Platelets have Functional Binding Sites for fVIII that are Distinct from Phosphatidylserine FVIII functions as a co-factor for fIXa on the membranes of stimulated platelets. Binding sites for fVIII are expressed at two levels; thrombin induces 3,000-20,000 sites/platelet while the combination of collagen and thrombin or A28137 induce >50,000 sites/platelet.

The inventors hypothesized that binding sites for fVIII on thrombin-stimulated platelets, are distinct from phosphatidylserine (PS), while those on maximally stimulated platelets are predominantly PS-containing sites. The hypothesis was based on the ideas that 1) epitopes on fVIII interact with the non-PS sites and 2) a macromolecule or a macromolecule complex comprises the binding sites on thrombin-stimulated platelets.

Methods

Platelets were purified on a discontinuous density gradient and binding of fluorescein-labeled fVIII (fVIII-fluor) to platelets and Superose beads was measured by flow cytometry using a Becton Dickinson LSR-Fortessa flow cytometer. FVIII activity was measured in a discontinuous factor Xase assay using extruded phospholipid vesicles of composition PS:PE:PC 4:20:76 or platelets as the membrane source. Oligomeric fibrin was immobilized by incubating thrombin, 1 u/ml, with fibrinogen, 10 µg/ml for 10 min without mixing prior to addition of 59D8-Superose beads. Binding of fVIII-4 Ala to platelets was measured in complex with Alexa-488 labeled mAb GMA-8021, against the A2 domain.

Results

Lactadherin, a phosphatidyl-L-serine-binding protein, competed for 97% of fVIII-fluorescein (fVIII-fluor) binding sites on A23187-stimulated platelets but only 30% of binding sites on thrombin-stimulated platelets. Unlabeled fVIII competed with fVIII-fluor for all binding sites. A fVIII C2 domain mutant, with no measurable phospholipid binding—M2199A/F2200A/L2251A/L2252A (fVIII-4Ala) bound to only 3,000-5,000 sites on platelets stimulated with A23187 but to a similar number on thrombin-stimulated platelets with a KD of 7 nM. These data indicate that non-PS sites are dominant on thrombin-stimulated platelets but that PS-containing sites comprise at least 95% of sites on A23187-stimulated platelets.

The inventors evaluated a panel of monoclonal antibodies (mAbs) against the fVIII-C2 domain for platelet-specific inhibition of binding and function. mAbs ESH4 and 154, with overlapping epitopes, blocked binding of fVIII to thrombin-stimulated platelets but only decreased affinity for PS-containing membranes. In 1-stage and 2-stage commercial aPTT assays ESH4 inhibited 28-33% of fVIII activity. In contrast, ESH4 inhibited 80% of fVIII activity on thrombin-stimulated platelets. mAb's ESH8 and G99, with partially overlapping epitopes decreased the affinity of fVIII-fluor for thrombin-stimulated platelets approx. 70% but had no effect on phospholipid binding ESH8 inhibited 58±8% of fVIII activity on thrombin-stimulated platelets but had no effect on activity supported by phospholipid vesicles.

Because oligomeric fibrin is required for expression of most fVIII binding sites on thrombin-stimulated platelets (Phillips et al 2004; JTH 2:1806) the inventors hypothesized that oligomeric, platelet-bound fibrin is a constituent of fVIII binding sites. fVIII-fluor bound to fibrin monomers and oligomers immobilized on mAb 59D8-Superose, detected in solution by flow cytometry. Both ESH4 and ESH8 monoclonal antibodies selectively interfere with fVIII binding to fibrin; it is noted that while ESH8 interferes with fVIII binding to fibrin, this antibody does not interfere with fVIII binding to vWF.

These data indicate that thrombin-stimulated platelets bind fVIII via a non-PS binding site and that the binding is mediated by epitopes that have greater functional importance on platelets than on phospholipid vesicles. Platelet-bound oligomeric fibrin is a candidate for the non-PS binding site. These findings have clinical relevance to detection of inhibitory antibodies against fVIII.

TABLE 1

Effect of fibrin on parameters of factor Xase complex

|  | $K_M$ [fX] nM | $V_{Max}$ [fXa formed] nM/5 min. | $K_D$ Apparent fVIIIa <-> fIXa nM | $K_D$ Apparent [Phospholipid*] µM |
|---|---|---|---|---|
| Control + fibrin | 57 ± 10 | 2.5 ± 0.1 | 19 ± 2 | 37 ± 4 |
|  | 32 ± 5 | 3.7 ± 0.2 | 5 ± 1 | 32 ± 6 |

Parameters were evaluated in the presence or absence of 20 µg/ml fibrin. Fibrinogen was exposed to 0.1 unit/ml thrombin for 2 min prior to addition of hirudin. Concentrations of each component were varied to evaluate the $K_M$, $V_{Max}$, and apparent dissociation constants.
*Extruded phospholipid vesicles had composition of PS:PE:PC 4:20:76.

The inventors' data indicate that platelets have two classes of fVIII binding sites. Platelet stimulation by calcium ionophore, a non-physiologic agonist, leads to exposure of many binding sites comprised primarily of exposed phosphatidylserine. Platelets stimulated by thrombin, a physiologic agonist, have binding sites that are not comprised primarily of phosphatidylserine. FVIII activity supported by thrombin-stimulated platelets is inhibited to a different degree by some inhibitory antibodies than fVIII activity supported by platelets stimulated by calcium ionophore.

Lactadherin, a phosphatidyl-L-serine binding protein blocks binding of fVIII to greater than 95% of binding sites on calcium ionophore stimulated platelets but only 30% of sites on platelets stimulated by thrombin An engineered fVIII molecule (fVIII-4 Ala) has defective phospholipid binding. Yet this molecule retains binding to thrombin-stimulated platelets confirming that the binding sites are not comprised of phospholipid. It has 95% reduction in binding to platelets stimulated with calcium ionophore.

These data are consistent with a model where platelet-bound fibrin serves as the primary binding site for fVIII on thrombin-stimulated platelets.

Summary

The inventors' data indicate that fVIII binds to: (i) fibrinogen immobilized on anti-fibrinogen antibodies supported by Superose beads. The KD is approximately 2 nM; (ii) fVIII-4 Ala binds to immobilized fibrinogen with lower affinity, and (iii) fVIII binds to suspended fibrinogen, not influenced by binding to antibodies or to SUPEROSE™ agarose beads.

The data further indicate that fVIII binds to: Oligomeric fibrin bound to an anti-fibrin antibody supported by Superose beads.

In addition, the data further indicate that activity of pure fVIII is increased by fibrinogen when (i) fVIII is activated by factor Xa, without conversion of fibrinogen to fibrin; the degree of activation is 2-6 fold, and (ii) when fVIII is activated by thrombin and fibrinogen is converted to fibrin. Pure fVIII is not increased by fibrinogen when fVIII is cleaved and released from the fVIII:von Willebrand complex by thrombin.

The data further indicate that: (i) von Willebrand factor competes with fibrinogen for fVIII binding, and (ii) von Willebrand factor decreases the activity of fVIII in the presence of factor Xa with the degree of inhibition corresponding to the predicted binding of fVIII to von Willebrand factor.

This discovery establishes a distinct pathway for fVIII activation and function that does not rely on prior generation of thrombin and does not require the presence of membranes of high phosphatidylserine content.

Applications

Provided herein are methods and assays for measuring the biological activity of fVIII using platelets, or a platelet-like substance, to replace phospholipids as a membrane source. An assay of this nature provides a better indication of the biologically relevant activity of fVIII as compared to the standard fVIII assay that activates platelets using a non-physiological agonist (e.g., a calcium ionophore). Also provided herein are screening assays for agents that modulate fVIII activity (e.g., recombinant fVIII).

Example 2

Platelet Binding Sites for Factor VIII in Relation to Fibrin and Phosphatidylserine It is demonstrated herein that lactadherin competes for 20-25% of factor VIII binding sites on thrombin-stimulated platelets while unlabelled factor VIII competes for >70% of these sites. Thus, most factor VIII binding sites do not rely on exposed phosphatidylserine. LW-fibrin attached to Superose beads resembled platelets in having high affinity factor VIII binding that was prevented by von Willebrand factor. LMW-fibrin enhanced activity of factor VIII by 2-3 fold in a factor Xase assay. Anti-factor VIII C2 domain mAb's ESH4 and ESH8 inhibited the binding of factor VIII to fibrin, activity enhancement by fibrin, binding of factor VIII to platelets, and >90% of factor VIII activity in an activated platelet-based clotting assay. These results indicate that platelet-bound fibrin functions as a component of factor VIII binding sites and that activity on these sites is inhibited by antibodies in a qualitatively distinct manner.

Factor VIII binds to platelet membranes where it serves as a cofactor for the enzyme, factor IXa in the intrinsic factor Xase complex (1, 2), which converts the zymogen factor X to factor Xa (3, 4). The importance of the factor Xase complex is illustrated by the disease haemophilia, in which deficiency of factor VIII (haemophilia A) or factor IX (haemophilia B) leads to life-threatening bleeding. In spite of the central importance of factor VIII, the platelet membrane binding sites have been only partially characterized.

Factor VIII circulates in plasma in a non-covalent complex with von Willebrand factor (VWF). Binding is mediated by the same motifs that bind platelet and phospholipid membranes (5, 6). After dissociation from VWF, factor binds specifically to membranes containing phosphatidylserine (PS), which is exposed on the platelet membrane in response to stimulation by several agonists (1, 6). The residual uncertainty about the identity of platelet binding sites relates to the quantity of PS exposed following stimulation by physiologic agonists and the availability of specific reagents to block the exposed PS. Thrombin stimulates platelets to expose limited PS, resulting in an outer membrane composition of 1-4% PS (7, 8). This amount of PS may remain below the threshold to support the observed expression of 200-1600 binding sites/platelet (9, 10). The combination of thrombin and collagen, or higher concentrations of the calcium ionophore, A23187, lead to complete PS exposure with membrane composition estimated at 12-15% PS (7, 8). Under these conditions, PS is thought to be a critical component of most of the >10,000 factor VIII binding sites exposed per platelet (11, 12).

Factor VIII has a domain structure of A1-a1-A2-a2-B-a3-A3-C1-C2, where a1, a2 and a3 are spacer regions. (13) The C1 and C2 domains mediate membrane binding (14-18). The factor VIII C domains share similar sequence and structure with the C domains of factor V (19-21) and lactadherin (22)

a milk fat globule membrane protein. Like factor VIII, both factor V and lactadherin preferentially bind to phosphatidylserine-containing membranes (23, 24). The membrane-binding role of the protruding hydrophobic amino acids of the factor VIII (17), factor V (25, 26), and lactadherin (27) C2 domains has been confirmed by site-directed mutagenesis. A factor VIII mutant, factor VIII-4Ala, with hydrophobic spike amino acids changed (M2199A/F2200A, L2251A/L2252A) has less than 1% residual binding to and activity on synthetic, phosphatidylserine-containing membranes (17). This factor VIII mutant has been used in the present study to test the hypothesis the platelets have binding sites not determined by membrane phospholipid.

Binding of soluble fibrin to the $\alpha_{IIb}\beta_3$ integrin on thrombin-stimulated platelets increases the number of factor VIII binding sites by 3-8 fold (28). However, factor VIII did not bind to fibrin adsorbed to polystyrene beads, indicating that factor VIII (i) does not bind directly to fibrin, (ii) the fibrin binding site was altered by contact with polystyrene, or (iii) that fibrin must be bound to the $\alpha_{IIb}\beta_3$ integrin. Described herein is the evaluation of the possibility that factor VIII(a) may bind directly to fibrin and that platelet-bound fibrin may be a component of the platelet binding sites for factor VIII.

Haemophilia A is treated by infusing purified plasma factor VIII into deficient patients. However, such treatment can result in the production of antibodies against factor VIII that impair function (29). Nearly half of inhibitory antibodies are directed against the C2 domain and many interfere with binding to phospholipid membranes and VWF. Monoclonal antibodies directed against the C2 domain mimic clinical inhibitory antibodies (30). ESH4 and ESH8 are two prototype anti-C2 antibodies with non-overlapping epitopes (31). ESH4 partially blocks binding to phosphatidylserine-containing membranes and binding to von Willebrand factor (30, 32). ESH8 doesn't inhibit factor VIII activity supported by PLV (32, 33), but slows the dissociation of activated factor VIII from von Willebrand factor (33). Described herein is the evaluation of the effect of ESH4 and ESH8 on factor VIII binding to fibrin and platelets and the extent to which the inhibitory effect on platelet-based factor VIII activity differs from phospholipid vesicle-based activity.

Materials

Materials: Porcine brain phosphatidylserine (PS), egg phosphatidylethanolamine (PE), and egg phosphatidylcholine (PC) were purchased from Avanti Polar Lipids. Calcium ionophore A23187, OptiPrep, thrombin receptor agonist peptides (TRAP) for PAR1 (SFLLRNPNDKYQPF) and PAR4 (AYPGKF-amide) were purchased from Sigma Aldrich. Purified human fibrinogen (unless otherwise specified), factor X, factor Xa, factor IXa, and thrombin were purchased from Enzyme Research Labs. Factor VIII-free VWF, corn trypsin inhibitor, and human factor XIa were purchased from Haematologic Technologies. Chromogenic substrate (S-2765) was purchased from Diapharma. Monoclonal antibodies ESH4 and ESH8 were purchased from American Diagnostica. Antibody GMA-8021 was purchased from Green Mountain Antibodies. Polyclonal antibodies to fibrinogen (ab6666), fibronectin (ab299), plasminogen (ab6189), and VWF (ab96340) were from Abcam. Anti-fibrin fragment E polyclonal antibody (F4197-40) was purchased from US Biological. Another anti-fibrinogen antibody was from Dako (A0080).

Methods

Proteins: Lipid-free bovine lactadherin was purified as described (24). The factor VIII C2 domain (fVIII-C2) was produced, purified, and stored as described. (18) Factor VIII was labeled with fluorescein maleimide as described (11). The ratio of fluorescein:factor VIII ranged from 0.6/1 to 1.2/1 for studies in this report. GMA8021 was labeled with fluorescein isothiocyanate using a standard protocol.

Flow cytometry measurement of factor VIII binding to platelets. Platelets from human volunteers were purified as described (28) and diluted in Tyrode's buffer (138 mM NaCl, 2.7 mM KCl, 3.3 mM $NaH_2PO_4$, 1 mM $MgCl_2$, 1% dextrose, 0.2% bovine serum albumin, 15 mM HEPES, pH 7.4) Binding of fluorescein-labeled factor VIII was measured by flow cytometry as previously described using a Becton Dickinson LSR-Fortessa™ flow cytometer.

Factor VIII binding to fibrin: Polyclonal anti-fibrinogen and mAb 59D8 were covalently coupled to batches of cyanogen bromide-activated Superose™ beads with an antibody/Superose™ ratio of 1.25 mg/mL as described (34). Fibrinogen, 10 µg/ml, was incubated with the Superose™ beads for 20 min. at 22° C. with 1 u/mL thrombin. Hirudin (3 u/mL) was added and excess fibrin was removed by sedimenting the Superose beads 500 g×30 s. Fibrin-Superose™ beads were resuspended in 50 mM Tris pH 7.85, 150 mM NaCl, 0.01% Tween 80, 0.1% BSA in a 2:1 ratio with Optiprep and incubated with factor VIII-fluor and competitors or inhibitors as indicated. In some experiments factor VIII-fluor was mixed with mAb's ESH4 or ESH8, VWF, or factor VIII-C2 prior to mixing with Superose™-fibrin beads, as indicated. Bound factor VIII-fluor was evaluated by flow cytometry on an LSR-Fortessa™ flow cytometer. Data acquisition was triggered by forward light scatter values characteristic of Superose™ beads. Data was evaluated as the geometric mean fluorescence of the dominant population (typically >90% of events).

Factor VIII activity: Factor VIII activity in the factor Xase complex was measured with two-step amidolytic substrate assays as described (15). Phospholipid vesicles were prepared by high-pressure extrusion through two-stacked polycarbonate membranes with laser-etched pores as described (35). Added fibrinogen was activated with thrombin concurrently with the factor VIII. One and two-stage factor VIII activity was measured in an aPTT assay (Helena Labs, aPTT-SA reagent) and in a 2-stage chromogenic assay (DiaPharma). One stage assays were performed, according to package instructions, with the BBL fibrometer. The chromogenic assay was performed according to manufacturer instructions with chromogenic substrate development read on a VersaMax™ microplate reader in kinetic mode.

Activated platelet time clotting assay: Purified platelets (28) were mixed with factor VIII deficient plasma supplemented with 25 µg/mL corn trypsin inhibitor to give a composition of $1\times10^8$ platelets/ml. Various concentrations of factor VIII were mixed with 10% normal plasma in Tyrode's buffer lacking phosphate and incubated for 1 hr at 22° C. prior to evaluating factor VIII activity. For the activated platelet time assay, 100 µl of reconstituted platelet-rich-plasma was mixed with 100 µl of factor VIII±inhibitory antibody for 1 min at 37° C. The clotting reaction was started by adding 100 µl of a mixture containing fXIa (200 pM), TRAP-PAR1 (30 µM), TRAP-PAR4 (300 µM), and CaCl (15 mM) in phosphate-free Tyrode's albumin buffer. Fibrin strand formation was measured with a BBL fibrometers in 300 µl sample cups. Experiments were performed in triplicate.

Results

Figure 1B:
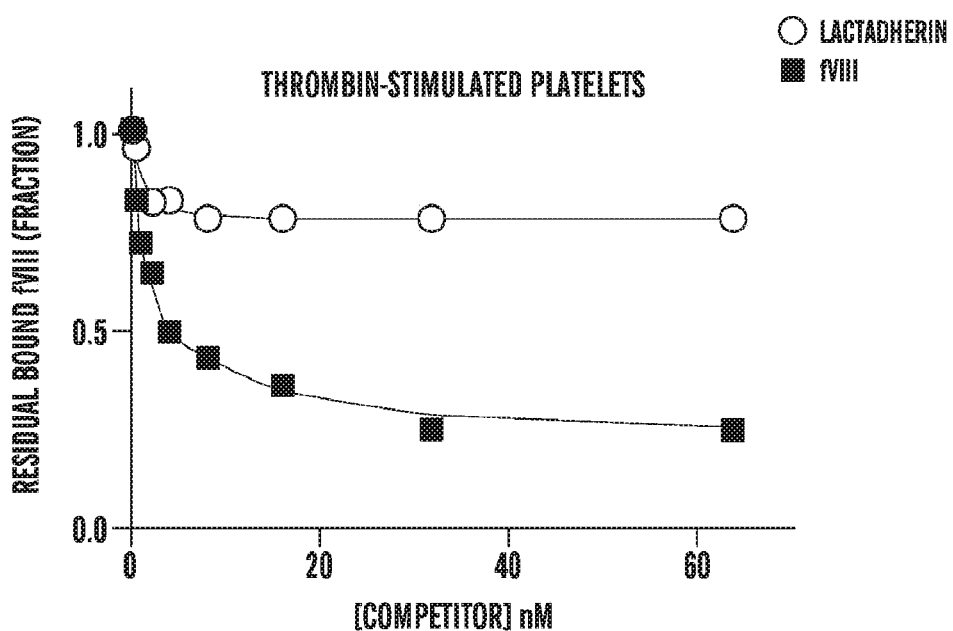

To test the hypothesis that platelets have non-phospholipid binding sites or receptors for factor VIII (9, 36), competition by lactadherin for factor VIII binding sites was evaluated (FIGS. 1A-1B). Factor VIII-fluor bound to many binding sites on platelets stimulated by A23187 and thrombin (FIG. 1A) consistent with the large number of binding sites predicted from extensive PS exposure. Addition of lactadherin, at a concentration that blocks >99% of factor VIII binding to PS-containing synthetic membranes (35), blocked approx. 95% of factor VIII binding to stimulated platelets. However, factor VIII-fluor still bound saturably to approx. 5% of binding sites, corresponding to more than 1,000 sites/platelet. This indicates that PS is not a critical component of 3-5% of the sites.

Thrombin, without A23187, stimulated expression of 450-1800 binding sites, as previously reported (28). Lactadherin competed for 20-25% of these binding sites (FIG. 1B) indicating that PS is a critical component of some binding sites, consistent with the previously reported limited PS exposure (7, 8, 37, 38). In contrast to lactadherin, unlabeled factor VIII competed for >70% of factor VIII binding sites, indicating specific sites for factor VIII that don't rely on PS.

Figure 2A:
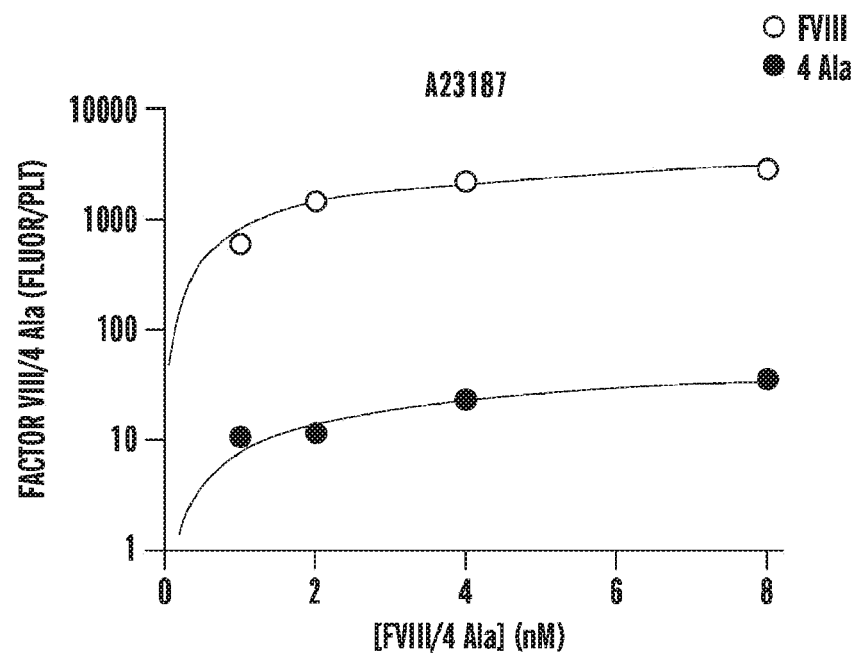
FIGS. 2A-2B are line graphs showing binding of fVIII 4-Ala to platelets stimulated by 10 μM A23187+ thrombin or by thrombin alone. The number of sites recognized by fVIII 4-Ala is reduced approximately 99% on A23187+ thrombin-stimulated platelets but by approximately 40% on thrombin-stimulated platelets.
Figure 2B:
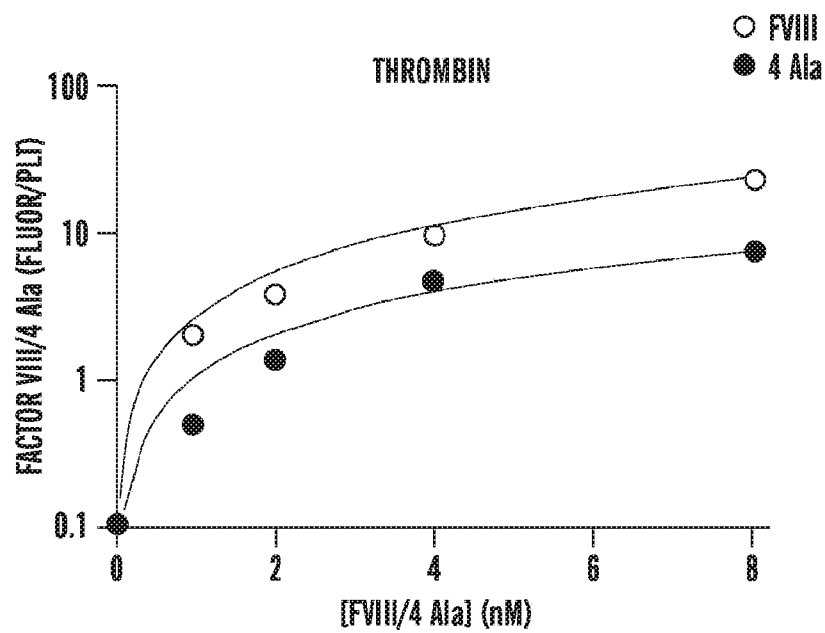
Figure 3A:
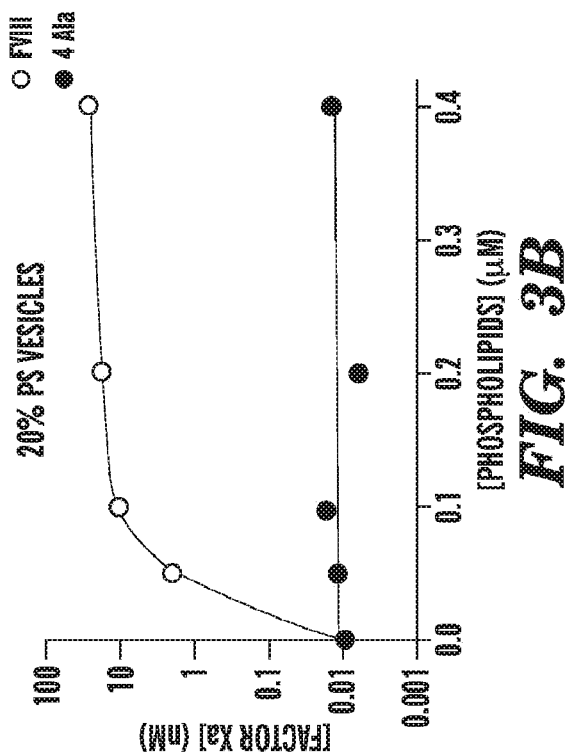
FIGS. 3A-3D are line graphs showing activity of fVIII 4-Ala on platelets vs. phosphatidyl-L-serine (Ptd-L-Ser) vesicles. Platelets were stimulated with A23187 and thrombin (FIG. 3A) or thrombin alone (FIG. 3C) and the supported activity of fVIII evaluated in a factor Xase assay. By comparison, the activity of fVIII and fVIII 4-Ala was evaluated in factor Xase assays supported by vesicles with 20% Ptd-L-Ser (FIG. 3B) or with 4% Ptd-L-Ser (FIG. 3D). fVIII 4-Ala supports approximately 5% residual activity on A23187+ thrombin-stimulated platelets, approximately 10% residual activity on thrombin-stimulated platelets. No residual activity was detected on vesicles with 20% Ptd-L-Ser or 4% Ptd-L-Ser.
Figure 3B:
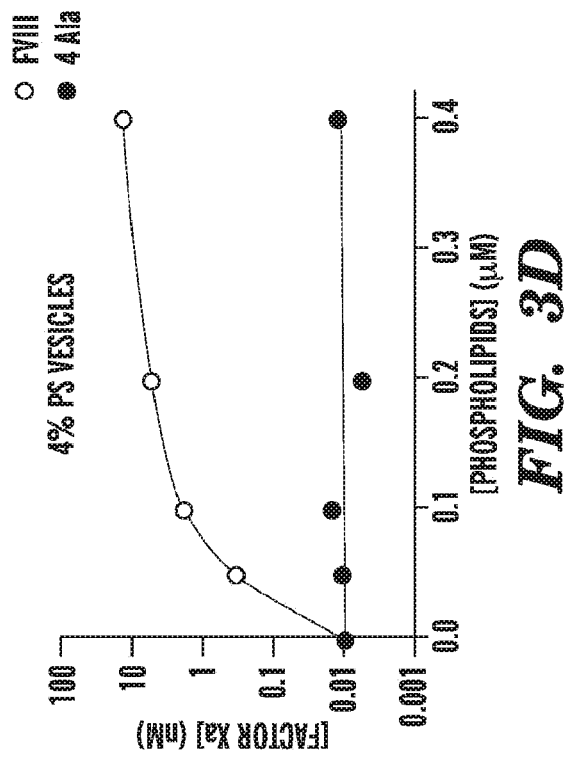
Figure 3C:
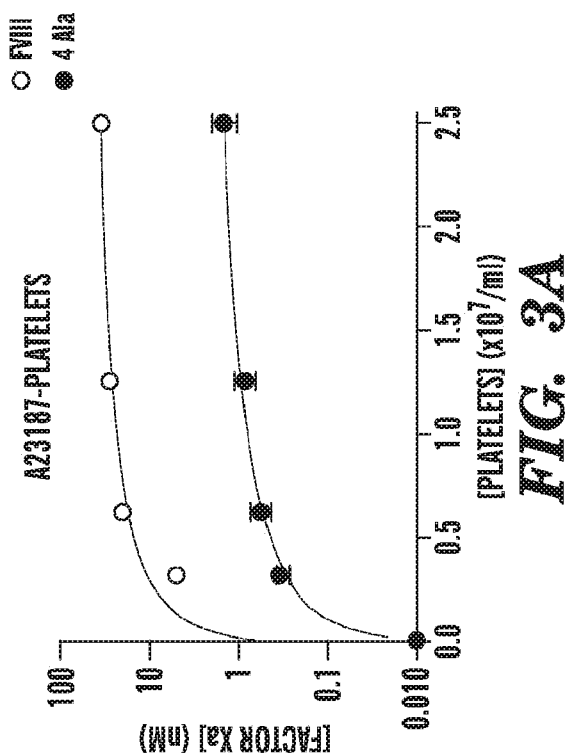
Figure 3D:
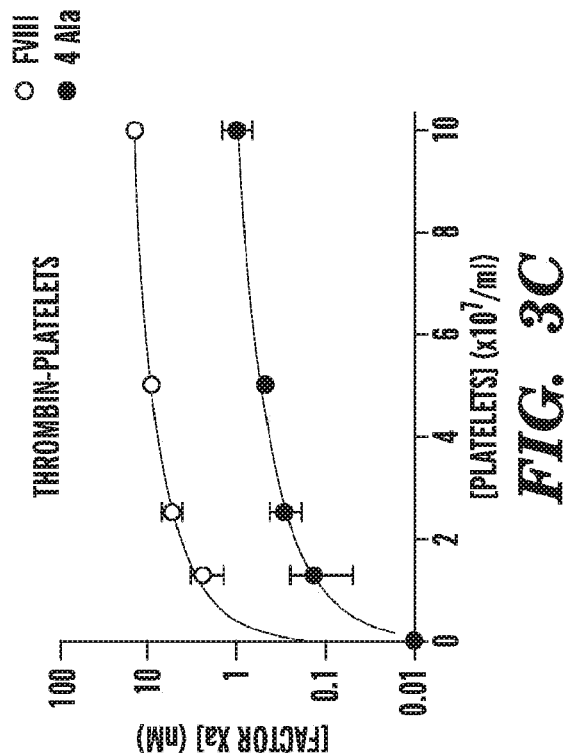

Binding of a factor VIII mutant with defective phospholipid binding was evaluated. Factor VIII-4Ala (M2199A/F2200A, L2251A/L2252A) has <1% residual phospholipid membrane affinity (17) (FIGS. 2A-2B). Binding of factor VIII-4Ala was reduced approx. 99% on platelets stimulated with A23187 and thrombin (FIG. 2A). In contrast, factor VIII-4Ala bound to approx. 50% of binding sites on platelets stimulated by thrombin (FIG. 2B). These results confirm that the phospholipid binding motif of the factor VIII C2 domain is not critical for at least 50% of binding sites on thrombin-stimulated platelets.

Figure 4A:
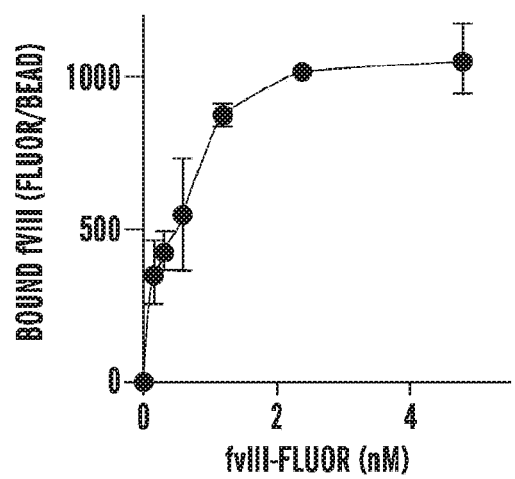
FIGS. 4A-4C depict the binding of factor VIII to fibrin.
Figure 10A:
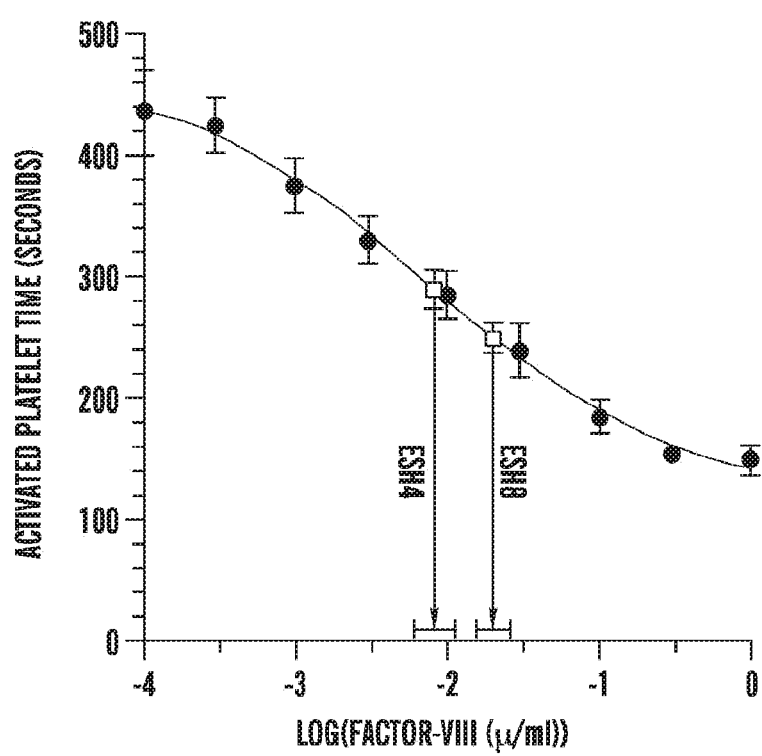
FIGS. 10A-10C demonstrate the effect of ESH4 and ESH8 on activity of factor VIII with activated platelets and phospholipid vesicles.
Figure 10B:
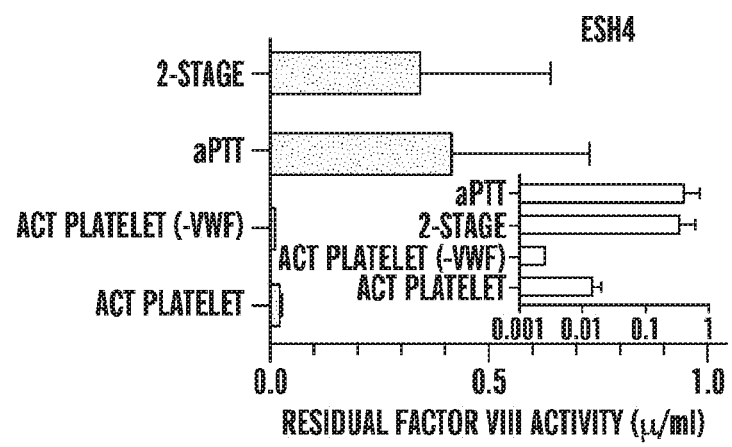
Figure 10C:
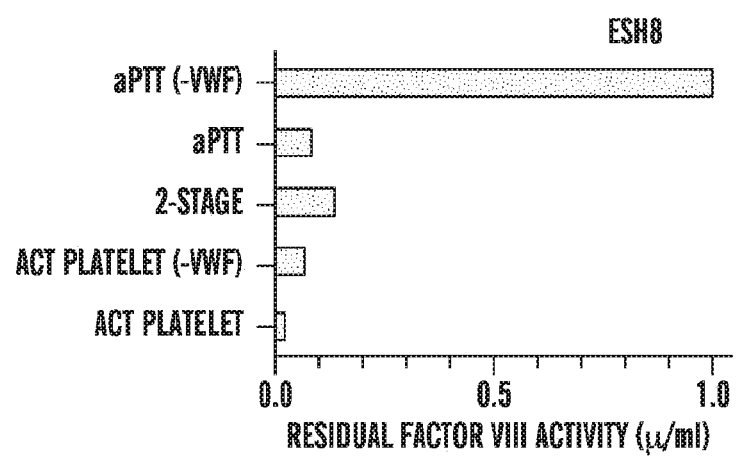

Binding of soluble fibrin to the $\alpha_{IIb}\beta_3$ integrin results in a 3-6 fold increase in factor VIII binding sites on thrombin-stimulated platelets (28). It was asked whether soluble fibrin bound to a platelet might serve as a binding site (FIGS. 10A-10C). Accordingly, soluble fibrin (39) was prepared in the presence of anti-fibrinogen antibodies coupled to Superose™. Immobilization of fibrin was verified with a fluorescein-labeled an anti-fibrinogen/anti-fibrin antibody. Factor VIII-fluor bound to fibrin-Superose with half-maximal binding at 1-2 nM (FIG. 4A). Factor VIII-fluor bound to fibrin with similar affinity when fibrin was immobilized on Superose-59D8, an antibody n-terminus of the fibrin β chain (40) confirming that fibrin binds factor VIII. Factor VIII-4Ala also bound to immobilized fibrin (data not shown). The quantity bound was approx. 50% of wild type factor VIII at 2 nM. These data indicate that factor VIII binds to fibrin and that the fibrin-interactive residues differ from those that are critical for binding to PS-containing membranes.

Figure 4B:
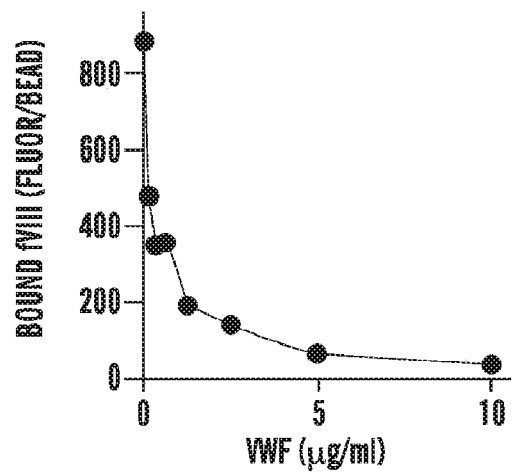
Figure 4C:
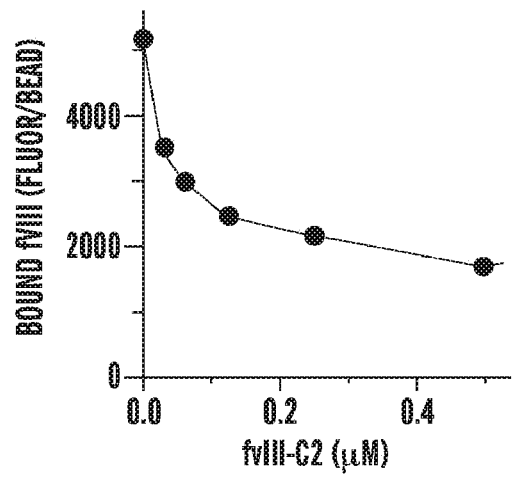

VWF prevented binding of factor VIII to immobilized fibrin, similar to inhibition of factor VIII binding to thrombin-stimulated platelets (FIG. 4B) (5). Because factor VIII binding to platelets and to VWF is mediated, in part, by the C2 domain it was asked whether the isolated C2 domain (fVIII-C2) competes with factor VIII for binding to fibrin (FIG. 4C). FVIII-C2 competed with factor VIII for binding to fibrin with 50% competition at approx. 0.1 μM factor VIII-C2. The competition studies with factor VIII-C2 were performed in a low salt buffer, similar to buffer conditions required for fVIII-C2 to bind phospholipid membranes (18). These results indicate that factor VIII binding to fibrin is similar to binding to platelets with regard to affinity, prevention by VWF and participation of the C2 domain.

Figure 5A:
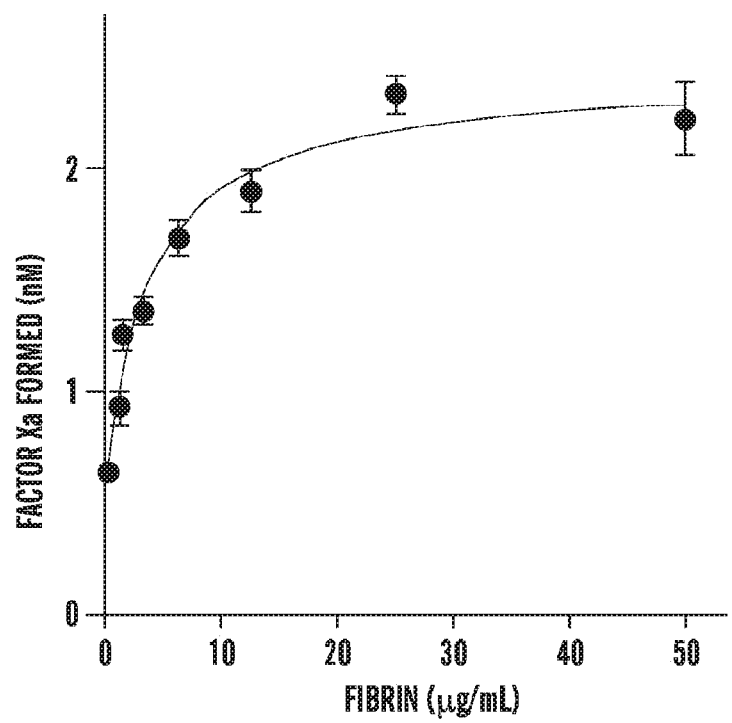
FIGS. 5A-5B show the effect of fibrin on function of fVIII.
Figure 5B:
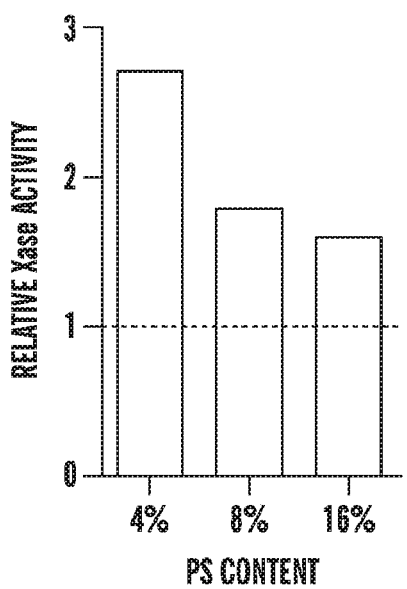

Because factor VIII binds to soluble fibrin it asked what effect fibrin has on the activity of factor VIII (FIGS. 5A-5B). Soluble fibrin increased activity of the factor Xase complex approx. 2.7-fold with a half-maximal increase at 5-10 μg/ml fibrin (FIG. 5A). At fibrin concentrations exceeding 200 μg/ml factor Xase activity decreased (not shown) reaching baseline at approx. 500 μg/ml. The size of the fibrin enhancement was inversely related to the PS content of PLV's supporting the reaction (FIG. 5B). The degree of enhancement was 2.7-fold on PLV with 4% PS and 1.8-fold or less on PLV with 8% and 16% PS. These results indicate that soluble fibrin increases factor Xase activity on PLV with PS content similar to thrombin-stimulated platelets.

The constituents of the factor Xase complex were varied systematically to determine which steady state kinetic parameters of the factor Xase complex were altered (Table I). The results indicated that soluble fibrin increases the apparent affinity of factor VIIIa for factor IXa by about 4-fold. In addition, the $V_{max}$ increased by 50% and the $K_M$ decreases by about 50%. Thus, the largest effect on parameters of steady state kinetics is on the apparent affinity of factor VIIIa for factor IXa.

The data presented herein indicates that soluble fibrin has relatively few binding sites that increase factor VIII activity. Maximal enhancement of factor VIII activity occurs with a fibrin monomer/factor VIII ratio of approx. 10-30 (FIG. 5A). Modifying the experimental protocol to increase or decrease the size of soluble fibrin units by 2-6 fold did not affect the effective concentration (data not shown). Thus, it appears that the ratio of fibrin monomer/factor VIII activity enhancing site is determined by a unique property of a small fraction of fibrinogen molecules.

Figure 6A:
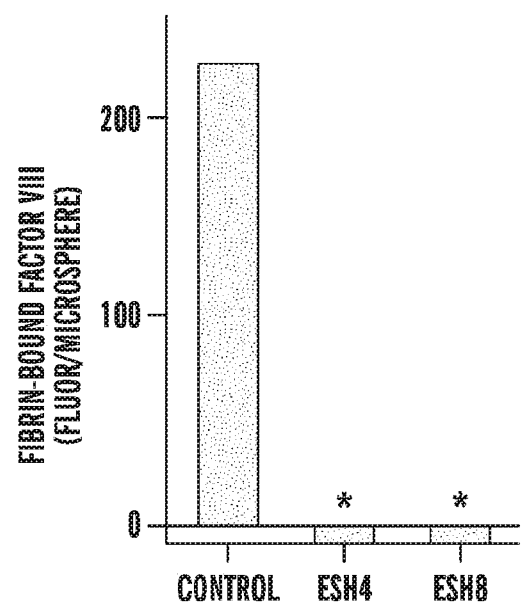
FIGS. 6A-6B demonstrate the effect of anti-factor VIII mAb's on factor VIII binding to fibrin.
Figure 6B:
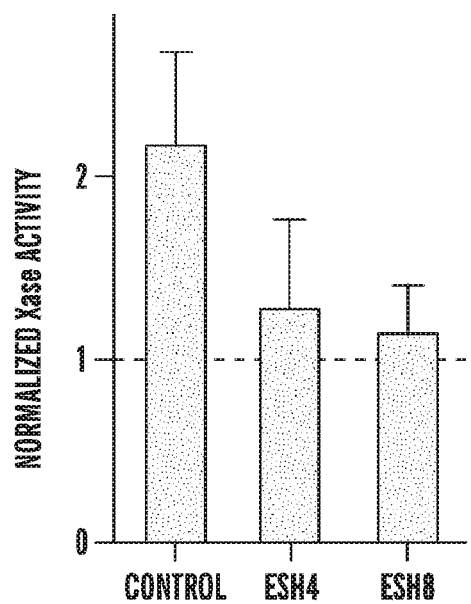

Because the C2 domain is implicated in binding to fibrin by the data presented herein, it was asked whether mAb's against the C2 domain inhibit this interaction (FIG. 6A). Both ESH8 and ESH4 inhibit factor VIII binding to fibrin (FIG. 6A). It was then tested whether the antibodies blocked the fibrin-mediated increase in factor Xase activity (FIG. 6B). ESH4 decreased, but did not entirely prevent, activity supported by PLV, as previously observed (15). However, the residual activity in the presence of ESH4 was not enhanced by addition of soluble fibrin (FIG. 6B). As previously reported, ESH8 did not inhibit factor VIII activity in the absence of fibrin (33) but did prevent the increase mediated by fibrin (FIG. 6B).

Figure 7C:
FIGS. 7A-7C demonstrate the effect of ESH4 and ESH on factor VIII binding to thrombin-stimulated platelets.
Figure 7B:
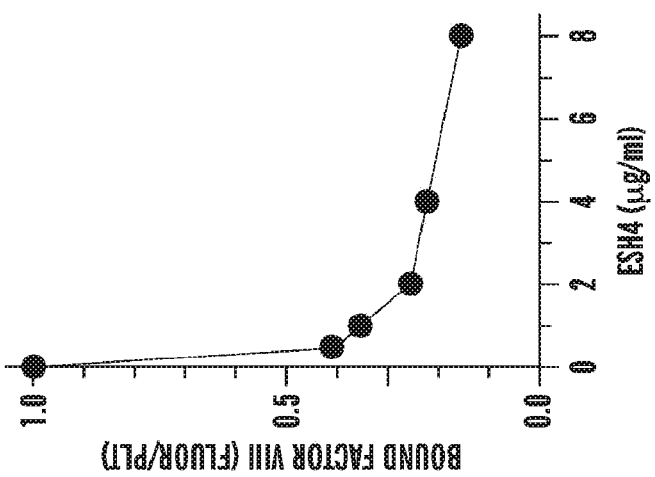
Figure 7A:
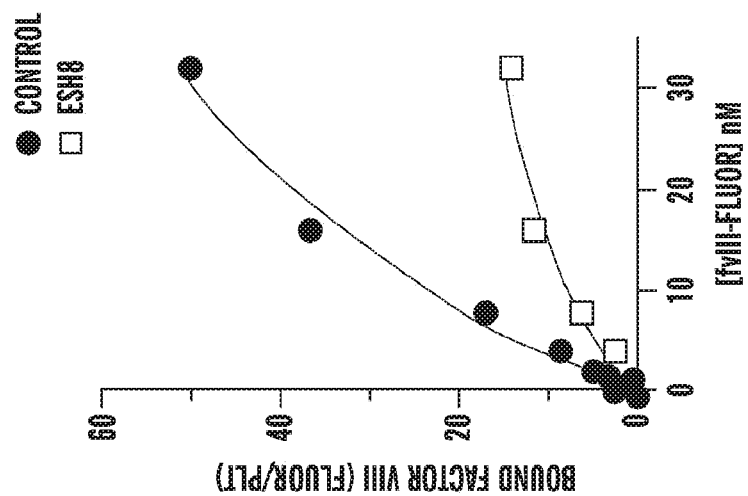
Figure 8:
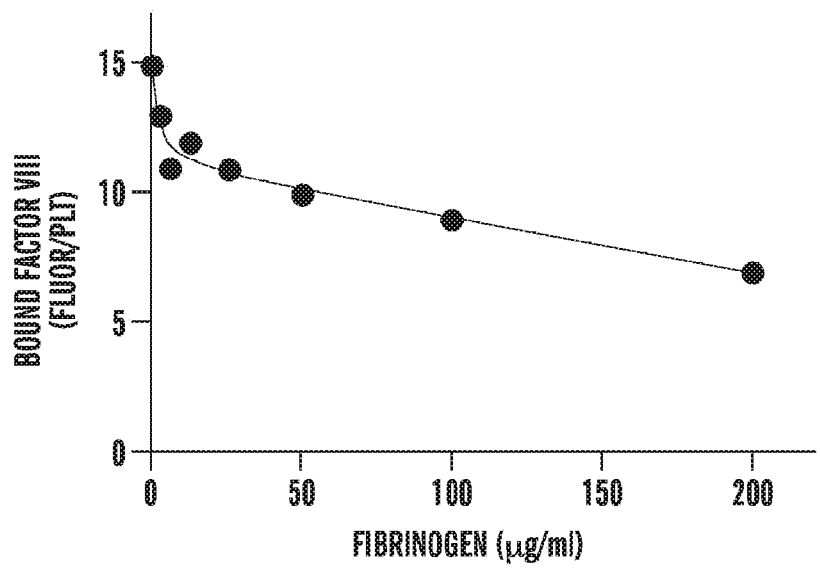
FIG. 8 is a graph showing the amount of bound fVIII at different concentrations of fibrinogen. FVIII was incubated with thrombin-stimulated platelets in the presence and absence of various concentrations of fibrin(ogen). Increased concentrations of fibrinogen decreased fVIII bound to platelets.
Figure 9:
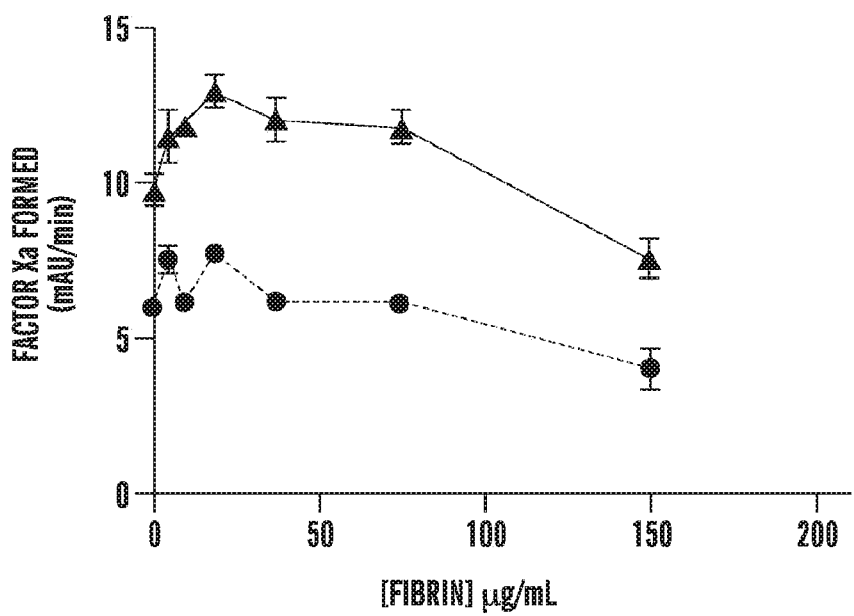
FIG. 9 is a graph showing the amount of factor XA formed at increasing concentrations of fibrin. Platelets were stimulated with thrombin and the thrombin blocked by hirudin. The platelet-supported factor Xase activity was measured in the presence of fVIII, factor IXa and factor X. The reaction was initiated by the addition of 1 nM factor Xa and terminated after 10 min by addition of EDTA. Factor Xa formed was measured with chromogenic substrate. Lower concentrations of fibrin increased factor Xase activity while higher concentrations decreased activity.

ESH8 decreased the number of binding sites recognized by factor VIII on thrombin stimulated platelets by approx. 70% (FIG. 7A) similar to the non-phospholipid fraction of binding sites (FIG. 1B). ESH4 also inhibited factor VIII binding to thrombin-stimulated platelets (FIG. 7B). The degree of inhibition was greater, consistent with the capacity of ESH4 to decrease affinity for PS-containing membranes (33) as well as fibrin. ESH8 inhibited 80% of platelet-dependent factor Xase activity (FIG. 7C). In a similar manner, ESH4 decreased activity by 70-85%. Thus, the inhibition of factor Xase activity parallels the inhibition of factor VIII binding to thrombin-stimulated platelets. However, the inhibition of platelet-based activity by ESH8 is in marked contrast with its lack of inhibition of factor VIII activity supported by PS-containing membranes (33).

To evaluate the importance of the ESH4 and ESH8 epitopes in a more physiologic system an activated platelet clotting time was developed (FIGS. 10A-10C). Purified platelets were re-constituted with factor VIII-deficient plasma supplemented with various concentrations of factor VIII. The reaction was initiated by simultaneous addition of factor XIa, thrombin receptor activation peptides for PAR1 and PAR4, and $Ca^{++}$. The results indicated a log-linear relationship between factor VIII concentration and time to fibrin strand formation over a wide factor VIII concentration range (FIG. 10A). When ESH8 was incubated with 1 u/ml factor VIII the delay in fibrin strand formation was consistent with a 97% reduction in factor VIII activity (FIGS. 10A, 10C). Because ESH8 inhibits release of factor VIIIa from VWF (33), experiments with ESH8 were also performed with VWF-deficient plasma. ESH8 inhibited 93% of factor VIII activity in the absence of plasma VWF. This contrasts with the degree of inhibition by ESH8 in standard aPTT and 2-stage factor VIII activity assays (FIG. 10C) where there is less inhibition in the presence of VWF and no inhibition in the absence of VWF.

ESH4 inhibited 99% of factor VIII activity in the activated platelet time assay (FIG. 10A). In contrast, the degree of inhibition ranged from 30% to 70% in commercial aPTT and 2-stage assays (FIG. 10B). When ESH4 was incubated with factor VIII in VWF-deficient plasma the degree of inhibition was 99.7% (FIG. 10B-inset). Without wishing to be bound by theory, ESH4 and VWF may compete for overlapping epitopes on factor VIII and VWF likely protected a fraction of factor VIII from interacting with ESH4. Overall, the results indicate that the degree of inhibition in a platelet and plasma-based system is better predicted by factor VIII binding to platelets and to fibrin than to phospholipid vesicles.

Discussion

The data presented herein demonstrate that stimulated platelets have factor VIII(a) binding sites that are distinct from membrane PS. Factor VIII binds to soluble fibrin and the binding characteristics of that interaction parallel the interaction with the non-PS binding sites of platelets. Notably, factor VIII has similar affinity for fibrin and binding is blocked by VWF in a similar manner. Further, inhibition of factor VIII binding to fibrin predicts the inhibitory activity of two monoclonal antibodies to factor VIII in platelet-based assays. Thus, they support a hypothesis that platelet-bound fibrin is a component of non-PS platelet binding sites.

It is demonstrated herein that lactadherin, a PS-binding protein that competes for >99% of sites recognized by factor VIII (35), does not compete for most sites on thrombin-stimulated platelets. Further, it is demonstrated herein that a factor VIII mutant with severely impaired phospholipid affinity (17) retains binding to thrombin-stimulated platelets.

Without wishing to be bound by theory, it is contemplated herein that PS is not necessarily required for full activity of factor VIII. Although lactadherin did not compete for a class of factor VIII binding sites, it did diminish activity by >99%, as previously reported (38).

Soluble fibrin binding to the $\alpha_{IIb}\beta_3$ integrin of platelets increases binding sites for factor VIIIa (28). Fibrin adsorbed to polystyrene beads had no detectible binding to factor VIII. As described herein, soluble fibrin bound to an antibody on a porous Superose matrix does bind factor VIII. Without wishing to be bound by theory, it is contemplated herein that soluble fibrin bound to the $\alpha_{IIb}\beta_3$ integrin may support factor VIII binding. The binding to these sites was diminished when beads were sedimented in multiple washes. This indicates that the binding surfaces can adhere to other fibrin molecules or are subject to conformational change.

In the absence of VWF, ESH8 doesn't inhibit activity of factor VIII on PS-containing membranes (33). Thus, inhibition of factor VIII binding to fibrin (FIGS. 6A-6B), inhibition of factor VIII binding to platelets (FIG. 7A) and inhibition of platelet-based procoagulant activity (FIGS. 10A-10C) appear to identify a distinct function of the ESH8 epitope that has not been reported.

The importance of the ESH4 epitope for membrane binding is modest when the PS content of vesicles is above 15% (15). Thus, it is not surprising that ESH4 causes only modest inhibition of factor VIII activity in the commercial 1 and 2-stage factor VIII activity assays that have saturating concentrations of phospholipid vesicles with high PS content (FIG. 10B). In contrast, ESH4 blocked binding to fibrin and >80% of binding sites on thrombin-stimulated platelets. This correlated to 85% reduction of platelet factor Xase activity (FIG. 10C) and 98-99% reduction of platelet procoagulant activity (FIG. 10B). In VWF-deficient plasma the inhibition of platelet procoagulant activity was greater. This indicates that the non-phospholipid factor VIII binding sites have greater importance in plasma coagulation than the 20-25% platelet binding sites that are mediated by phospholipid (FIG. 1B).

The activated platelet time assay utilized herein differs from a prior platelet-based coagulation assay in that platelets were activated at the outset of the reaction by peptides that stimulate platelets via PAR1 and PAR4 (42). The results with the present assay contrast with results from reported factor VIII assays. First, the range over which fibrin strand formation had a log-linear relationship of factor VIII concentration to coagulation time of 0.0003-0.3 units/ml. In contrast, established factor VIII assays have a factor VIII-time log-linear range of 0.01-0.3 units/ml (43). Thus, a coagulation assay based on the activated platelet membrane rather than phospholipid vesicles may have potential as the basis of a clinical assay with a broader range. In addition, the sensitivity of the assay to factor VIII inhibition by ESH4 and ESH8 differed by >10-fold compared to commercially available 1-stage and 2-stage assays. These data indicate that an assay in which factor VIII activity is supported by the activated platelet membrane can provide clinical information for patients who have developed inhibitor antibodies.

In summary, the data presented herein demonstrate that platelets have non-PS binding sites for factor VIII. Soluble fibrin is required to constitute these sites and fibrin binds factor VIII with properties that indicates that fibrin or a complex of fibrin with another molecule is the best candidate for the non-phospholipid site. Activity of factor VIII on the non-PS platelet sites has qualitatively different susceptibility to anti-factor VIII antibodies in a platelet-based coagulation assay.

Supplemental Data

Experiments with factor VIII-4Ala differed in that factor VIII-4Ala was labeled by incubation with mAb GMA8021-fluor for 1 hr at a ratio of 4:1. For these experiments wild type factor VIII was labeled in the same manner as a control. Recombinant factor VIII-4Ala was prepared by mutagenesis within the mammalian expression vector pMT2 as described (45). Conditioned medium from transfected COS-1 cells was harvested at 64 h post-transfection in the presence of 10% fetal bovine serum and purified by immunoaffinity chromatography as described (17). Each preparation yielded 1.5-3.0 µg of protein. The purified protein was stored at −70° C. until use. The factor VIII C2 domain was produced in *E. coli*, purified, and stored as described (18).

REFERENCES

1. Gilbert G E, Furie B C, Furie B. Binding of human factor VIII to phospholipid vesicles. J Biol Chem. 1990; 265: 815-22. PubMed PMID: 2104832.
2. Gilbert G E, Drinkwater D. Specific membrane binding of factor VIII is mediated by O-phospho-L-serine, a moiety of phosphatidylserine. Biochemistry. 1993; 32:9577-85. PubMed PMID: 8373765.
3. Mann K G, Nesheim M E, Church W R, Haley P, Krishnaswamy S. Surface-dependent reactions of the vitamin K-dependent enzyme complexes. Blood. 1990; 76:1-16.

4. Mertens K, Cupers R, Van Wijngaarden A, Bertina R M. Binding of human blood-coagulation factors IXa and X to phospholipid membranes. Biochem J. 1984; 223:599-605.
5. Nesheim M, Pittman D, Giles A, Fass D, Wang J, Slonosky D, et al. The Effect of Plasma von Willebrand Factor on the Binding of Human Factor VIII to Thrombin-Activated Human Platelets. J Biol Chem. 1991; 266(27): 17815-20.
6. Gilbert G E, Drinkwater D, Barter S, Clouse S B. Specificity of phosphatidylserine-containing membrane binding sites for factor VIII: Studies with model membranes supported by glass microspheres (Liposheres). J Biol Chem. 1992; 267(22):15861-8. PubMed PMID: 1639816.
7. Bevers E, Comfurius P, Van Rijn J, Hemker H, Zwaal R. Generation of Prothrombin-Converting Activity and the Exposure of Phosphatidylserine at the Outer Surface of Platelets. Eur J Biochem. 1982; 122(2):429-36.
8. Bevers E, Comfurius P, Zwaal R. Changes in membrane phospholipid distribution during platelet activation. Biochim Biophys Acta. 1983; 736:57-66.
9. Nesheim M E, Pittman D D, Wang J H, Slonosky D, Giles A R, Kaufman R J. The binding of $^{35}$S-labeled recombinant factor VIII to activated and unactivated human platelets. J Biol Chem. 1988; 263:16467-70.
10. Phillips J E, Gilbert G E. Platelet exposure of functional factor VIII binding sites requires stimulation by thrombin and shear stress. Blood. 1995; 86:549a.
11. Gilbert G E, Sims P J, Wiedmer T, Furie B, Furie B C, Shattil S J. Platelet-derived microparticles express high affinity receptors for factor VIII. J Biol Chem. 1991; 266:17261-68.
12. Comfurius P, Smeets E F, Willems G M, Bevers E M, Zwaal R F A. Assembly of the prothrombinase complex on lipid vesicles depends on the stereochemical configuration of the polar headgroup of phosphatidylserine. Biochemistry. 1994; 33(34):10319-24.
13. Vehar G, Keyt B, Eaton D, Rodriguez H, O'Brien D, Rotblat F, et al. Structure of human factor VIII. Nature. 1984; 312(5992):337.
14. Hsu T C, Pratt K P, Thompson A R. The factor VIII C1 domain contributes to platelet binding. Blood. 2008 Jan. 1; 111(1):200-8. PubMed PMID: 17916745.
15. Lu J, Pipe S W, Miao H, Jacquemin M, Gilbert G E. A membrane-interactive surface on the factor VIII C1 domain cooperates with the C2 domain for cofactor function. Blood. 2011 Dec. 14; 117(11):3181-89. PubMed PMID: 21156843.
16. Meems H, Meijer A B, Cullinan D B, Mertens K, Gilbert G E. Factor VIII C1 domain residues Lys 2092 and Phe 2093 contribute to membrane binding and cofactor activity. Blood. 2009 Aug. 17; 114(18):3938-46. PubMed PMID: 19687511. Epub 2009/08/19. Eng.
17. Gilbert G E, Kaufman R J, Arena A A, Miao H, Pipe S W. Four hydrophobic amino acids in the factor VIII C2 domain are constituents of the membrane-binding and von Willebrand factor-binding motif. J Biol Chem. 2002 Feb. 22; 277(8):6374-81. PubMed PMID: 11698391.
18. Novakovic V A, Cullinan D B, Wakabayashi H, Fay P J, Baleja J D, Gilbert G E. Membrane-binding properties of the Factor VIII C2 domain. Biochem J. 2011 Apr. 1; 435(1):187-96. PubMed PMID: 21210768.
19. Church W R, Jernigan R L, Toole J, Hewick R M, Knopf J, Knutson G J, et al. Coagulation factors V and VIII and ceruloplasmin constitute a family of structurally related proteins. Proc Natl Acad Sci, USA. 1984; 81(22):6934-7.
20. Gitschier J, Wood W I, Goralka T M, Wion K L, Chen E Y, Eaton D H, et al. Characterization of the human factor VIII gene. Nature. 1984; 312(5992):326-30.
21. Toole J J, Knopf J L, Wozney J M, Sultzman L A, Buecker J L, Pittman D D, et al. Molecular cloning of a cDNA encoding human antihemophilic factor. Nature. 1984; 312(5992):342-7.
22. Stubbs J, Lekutis C, Singer K, Bui A, Yuzuki D, Srinivasan U, et al. cDNA cloning of a mouse mammary epithelial cell surface protein reveals the existence of epidermal growth factor-like domains linked to factor VIII-like sequences. Proc Natl Acad Sci, USA. 1990; 87:8417-21.
23. Krishnaswamy S, Mann K The Binding of Factor Va to Phospholipid Vesicles. J Biol Chem. 1988; 263:5714-23.
24. Andersen M H, Graversen H, Fedosov S N, Petersen T E, Rasmussen J T. Functional analyses of two cellular binding domains of bovine lactadherin. Biochemistry. 2000; 39(20):6200-6. PubMed PMID: 10821695.
25. Kim S W, Quinn-Allen M A, Camp J T, Macedo-Ribeiro S, Fuentes-Prior P, Bode W, et al. Identification of functionally important amino acid residues within the C2-domain of human factor V using alanine-scanning mutagenesis. Biochemistry. 2000; 39(8):1951-8.
26. Ortel T, Devore-Carter D, Quinn-Allen M, Kane W. Deletion analysis of recombinant human factor V: Evidence for a phosphatidylserine binding site in the second C-type domain. J Biol Chem. 1992; 267:4189-98.
27. Shao C, Novakovic V A, Head J F, Seaton B A, Gilbert G E. Crystal structure of lactadherin C2 domain at 1.7A resolution with mutational and computational analyses of its membrane-binding motif. J Biol Chem. 2008 Mar. 14; 283(11):7230-41. PubMed PMID: 18160406.
28. Phillips J E, Lord S T, Gilbert G E. Fibrin stimulates platelets to increase factor VIIIa binding site expression. J Thromb Haemost. 2004 doi 10.1111/j.1538-7836.2004.00919.x; 2(10):1806-15. PubMed PMID: 15456493.
29. Hoyer L W, Scandella D. Factor VIII inhibitors: structure and function in autoantibody and hemophilia A patients. Semin Hematol. 1994 April; 31(2 Suppl 4):1-5. PubMed PMID: 7524160.
30. Meeks S L, Healey J F, Parker E T, Barrow R T, Lollar P. Antihuman factor VIII C2 domain antibodies in hemophilia A mice recognize a functionally complex continuous spectrum of epitopes dominated by inhibitors of factor VIII activation. Blood. 2007 Dec. 15; 110(13): 4234-42. PubMed PMID: 17848617.
31. Griffin B D, Micklem L R, McCann M C, James K, Pepper D S. The production and characterisation of a panel of ten murine monoclonal antibodies to human procoagulant factor VIII. Thromb Haemost. 1986 Feb. 28; 55(1):40-6. PubMed PMID: 3085263.
32. Pipe S W, Kaufman R J. Characterization of a genetically engineered inactivation-resistant coagulation factor VIIIa. Proc Natl Acad Sci, USA. 1997 Oct. 28; 94(22):11851-6. PubMed PMID: 9342326. Pubmed Central PMCID: 23634.
33. Saenko E L, Shima M, Gilbert G E, Scandella D. Slowed release of thrombin-cleaved factor VIII from von Willebrand factor by a monoclonal and a human antibody is a novel mechanism for factor VIII inhibition. J Biol Chem. 1996; 271:27424-31.
34. Bendetowicz A V, Wise R J, Gilbert G E. Collagen-bound von Willebrand factor has reduced affinity for factor VIII. J Biol Chem. 1999 Apr. 30; 274(18):12300-7. PubMed PMID: 10212199.

35. Shi J, Gilbert G E. Lactadherin inhibits enzyme complexes of blood coagulation by competing for phospholipid binding sites. Blood. 2003 Apr. 1; 101(7):2628-36. PubMed PMID: 12517809.

36. Nesheim M E, Furmaniak-Kazmierczak E, Henin C, Cote G. On the existence of platelet receptors for Factor-V(a) and Factor-VIII(a). Thromb Haemost. 1993; 70(1): 80-6.

37. Rosing J, van Rijn J, Bevers E, van Dieijen G, Comfurius P, Zwaal R. The role of activated human platelets in prothrombin and factor X activation. Blood. 1985; 65:319-32.

38. Shi J, Pipe S W, Rasmussen J T, Heegaard C W, Gilbert G E. Lactadherin blocks thrombosis and hemostasis in vivo: correlation with platelet phosphatidylserine exposure. J Thromb Haemost. 2008 July; 6(7):1167-74. PubMed PMID: 18485093.

39. Alkjaersig N, Fletcher A P. Formation of soluble fibrin oligomers in purified systems and in plasma. Biochem J. 1983 Jul. 1; 213(1):75-83. PubMed PMID: 6615433.

40. Hui K Y, Haber E, Matsueda G R. Monoclonal antibodies to a synthetic fibrin-like peptide bind to human fibrin but not fibrinogen. Science. 1983 Dec. 9; 222(4628): 1129-32. PubMed PMID: 6648524. Epub 1983/12/09. eng.

41. Ono M, Matsubara J, Honda K, Sakuma T, Hashiguchi T, Nose H, et al. Prolyl 4-hydroxylation of alpha-fibrinogen: a novel protein modification revealed by plasma proteomics. J Biol Chem. 2009 Oct. 16; 284(42):29041-9. PubMed PMID: 19696023. Pubmed Central PMCID: 2781450.

42. Mikaelsson M, Oswaldsson U, Sandberg H. Influence of phospholipids on the assessment of factor VIII activity. Haemophilia. 1998 July; 4(4):646-50. PubMed PMID: 9873808.

43. Lollar P. The factor VIII assay problem: neither rhyme nor reason. J Thromb Haemost. 2003 November; 1(11): 2275-9. PubMed PMID: 14629457.

44. Egler C, Albert T, Brokemper O, Zabe-Kuhn M, Mayer G, Oldenburg J, et al. Kinetic parameters of monoclonal antibodies ESH2, ESH4, ESH5, and ESH8 on coagulation factor VIII and their influence on factor VIII activity. J Mol Recognit. 2009 July-August; 22(4):301-6. PubMed PMID: 19266540.

45. Kaufman R J. Selection and coamplification of heterologous genes in mammalian cells. Meth Enzymol. 1990; 185:537-66.

What is claimed herein:

1. A kit for measuring fVIII activity, the kit comprising:
fibrin or fibrinogen;
a platelet membrane-comprising composition;
Factor IXa;
Factor X;
a solid support having monoclonal antibodies that specifically bind fVIII immobilized thereupon; and
packaging materials therefor.

2. The kit of claim 1 further comprising a chromogenic fXa substrate.

3. The kit of claim 1 wherein said fibrin or fibrinogen is in association with said platelet membrane-comprising composition.

4. The kit of claim 1, wherein said platelet membrane-comprising composition comprises activated gpIIbIIIa incorporated into a membrane composition.

5. The kit of claim 1, further comprising instructions for a method of measuring fVIII activity, wherein the method comprises the steps of: contacting a sample in which fVIII is to be measured with (i) fibrin or fibrinogen and (ii) a platelet membrane-comprising composition, under conditions that permit binding of fibrin or fibrinogen to said platelet membrane-comprising composition and permit binding of fVIII in said sample to said fibrin or fibrinogen, and detecting activity of said fVIII contacting is performed in the presence of Factor IXa (fIXa) and Factor X (fX).

6. The kit of claim 5, wherein the instructions further describe methods for detecting activity of fVIII comprising detecting cleavage of a chromogenic fXa substrate by fXa.

7. The kit of claim 5, wherein the instructions further describe a method of detecting activity of fVIII comprising a plasma-based clotting assay and/or use of a fibrometer and/or use of a thromboelastometry device.

* * * * *